(12) United States Patent
Pedersen et al.

(10) Patent No.: US 7,355,004 B2
(45) Date of Patent: Apr. 8, 2008

(54) PROTEIN LIPASE INHIBITOR FOR FLOUR AND DOUGH

(75) Inventors: Henrik Pedersen, Østbirk (DK); Charlotte Horsmans Poulsen, Brabrand (DK); Jørn Borch Søe, Mundelstrup (DK); Masoud Rajabi Zargahi, Åbyhøj (DK)

(73) Assignee: Danisco A/S, Copenhagen (DK)

( * ) Notice: Subject to any disclaimer, the term of this patent is extended or adjusted under 35 U.S.C. 154(b) by 159 days.

(21) Appl. No.: 11/090,908

(22) Filed: Mar. 25, 2005

(65) Prior Publication Data
US 2005/0255574 A1 Nov. 17, 2005

Related U.S. Application Data

(63) Continuation-in-part of application No. PCT/IB03/04585, filed on Sep. 26, 2003.

(60) Provisional application No. 60/431,209, filed on Dec. 5, 2002.

(30) Foreign Application Priority Data

Sep. 27, 2002 (GB) .................. 0222512.6
Oct. 10, 2002 (GB) .................. 0223674.3
Dec. 2, 2002 (GB) .................. 0228082.4

(51) Int. Cl.
*C12N 9/20* (2006.01)
*C07K 14/415* (2006.01)
*A21D 2/26* (2006.01)

(52) U.S. Cl. .................. 530/350; 530/375; 426/19; 435/198

(58) Field of Classification Search .............. 435/198; 530/350, 375; 426/19
See application file for complete search history.

(56) References Cited

U.S. PATENT DOCUMENTS

2003/0186345 A1    10/2003    Hortin

FOREIGN PATENT DOCUMENTS

| EP | 0 979 830 A | 2/2000 |
|---|---|---|
| WO | WO 94/04035 | 3/1994 |
| WO | WO 98/45453 | 10/1998 |
| WO | WO 00/32758 A | 6/2000 |
| WO | WO 01/42433 A | 6/2001 |
| WO | WO 01/66711 A | 9/2001 |

OTHER PUBLICATIONS

Li et al., NCBI (GenBank) record No. AAP80612, bread wheat protein (Triticum aestivum), submitted to NCBI on Jan. 22, 2002.*

(Continued)

*Primary Examiner*—Rebecca E. Prouty
*Assistant Examiner*—Rosanne Kosson
(74) *Attorney, Agent, or Firm*—Frommer Lawrence & Haug LLP; Thomas J. Kowalski; Angela M. Collison

(57) ABSTRACT

The present invention relates to the isolation of and characterization of a novel lipase inhibitor and its effect on different lipases. The present invention also relates to the use of a lipase inhibitor as a screen for lipases. The present invention also relates to the use of the inhibitor and/or lipases identified by a lipase inhibitor in food and/or feed technologies.

9 Claims, 9 Drawing Sheets

OTHER PUBLICATIONS

Result 3, Uniprot database search, alignment of SEQ ID No. 7 with the polypeptide of Li et al. (item U), Uniprot record No. Q7X9M4/ NCBI record No. AAP80612, searched and printed on Feb. 13, 2007.*

On-line calculation at ExPASy PeptideMass, polypeptide of Li et al. (item U), http://ca.expasy.org/cgi-bin/peptide-mass.pl, printed on Feb. 13, 2007.*

Guo et al., "Protein tolerance to random amino acid change", PNAS 101(25): 9205-9210, Jun. 2004.*

PCT Notification of Transmittal of the International Preliminary Examination Report (PCT Rule 71.21) for PCT/IB03/04585, Dated Jan. 28, 2005.

PCT Written Opinion (PCT Rule 66 ) for PCT/IB03/04585, Dated Oct. 29, 2004.

PCT Notification of Transmittal of the International Search Report or the Declaration (PCT Rule 44.1) for PCT/IB03/04585, Dated Sep. 27, 2004.

Andersen, et al.;Identification of several new classes of low-molecular-weight wheat gliadin-related proteins and genes;Theoretical and Applied Genetics, vol. 103,pp. 307-315, 2001.

Hisanori Tani, et al.; "Purification and Characterization of Proteinous Inhibitor of Lipase from Wheat Flour" J. AGRI. Food Chem, vol. 42, 1994, pp. 2382-2385.

Lie Ken Jie, et al.; "Studies of Lipase-catalyzed esterfication reactions of some acetylenic fatty acids" LIPIDS. Jan. 1998, vol. 33, No. 1, Jan. 1998 pp. 71-75.

Ruiz, et al.; "Activation and Inhibition of Candida Rugosa and Bacillus-Related Lipases by Saturated Fatty Acids" BIOCHIMICA ET Biophysica, vol. 1672, No. 3, pp. 184-191, 2004.

Bitou, et al.; "Screening of Lipase Inhibitors from Marine Algae" LIPIDS, 1999, vol. 34, No. 5, May 1999, pp. 441-445.

* cited by examiner

Lane 1: Novex standard markers
Lane 7: Fraction 9 from the GFC, Superdex 75
Lane 8: Fraction 10 from the GFC, Superdex 75
Lane 9: Fraction 11 from the GFC, Superdex 75
Lane 10: Fraction 12 from the GFC, Superdex 75

(SEQ ID No. 7)

(SEQ ID No. 8)

```
  1 TTG GAA ACC ATA TGT AGC CAG GGC TTC GGA CAA TGC CAA CAC CAC CAA
 49 CAA CTA GGG CAA CAA CAG TTG CTG GAT CAG ATG AAG CCA TGT GTG GCT
 97 TTC GTA CAA CAT CAG TGT AGC CCA GTG AGA ACA CCA TTC CCC CAA ACA
145 CGG GGA GAG CAG CAT AGC AGT TGC CAA ACC GTG CAA CAC CAA TGC TGT
193 CGG CAG CTA GTG CAG ATC CCA GAA CAA GCC CGG TGC AAG GCC ATA CAG
241 AGC GTG GAA GAG GCT ATC ATT CAA CAA CAG CCC CAA CAA CAA TGG AAT
289 GAG CCC CAA CAG GAA GCA CAC CTT AAG AGC ATG AGG ATG TCG CTT CAG
337 ACC CTG CCG TCT ATG TGC AAC ATC TAC GTC CCG GTA CAA TGC CAG CAA
385 CAG CAA CAA CTG GGG CGA CAA CAA CAA CAA CAG TTG CAG GAG CAG TTA
433 AAA CCG TGT GCG ACA TTC CTA CAA CAT CAA TGT AGG CCA ATG ACA GTG
481 CCA TTC CCG CAT ACA CCA GTG CAG AAG CCC ACC AGC TGC AGA ACG TG
529 CAG TCC CAA TGC TGC CGG CAG CTA GCA CAG ATC CCA GAG CAA TTC CGC
577 TGC CAA GCC ATT CAT AAT GTG GTA GAG TCT ATC AGG CAA CAA CAA CAT
625 CAC CAA CCA CAA CAG GAA GTA CAA CTT GAG GGC CTG AGG ATG TCA CTT
673 CAC ACC CTA CCG TCG ATG TGC AAA ATC TAC ATC CCT GTA CAA TGC CCA
721 GCC ACC ACC ACC ACC CCC TAT AGC ATT ACC ATG ACA GCT AGC TAT ACC
769 GAT GGT ACC TGC TAG
```

Fig. 8

SEQUENCE LISTING

<160> NUMBER OF SEQ ID NOS: 8

<210> SEQ ID NO 1
<211> LENGTH: 35
<212> TYPE: PRT
<213> ORGANISM: Triticum sp.

<400> SEQUENCE: 1

Glu Pro Gln Gln Glu Ala His Leu Lys Ser Met Arg Met Ser Leu Gln
1               5                   10                  15

Thr Leu Pro Ser Met Cys Asn Ile Tyr Val Pro Val Gln Cys Gln Gln
            20                  25                  30

Gln Gln Gln
        35

<210> SEQ ID NO 2
<211> LENGTH: 24
<212> TYPE: PRT
<213> ORGANISM: Triticum sp.

<400> SEQUENCE: 2

Glu Thr Ile Cys Ser Gln Gly Phe Gly Gln Cys Gln His His Gln Gln
1               5                   10                  15

Leu Gly Gln Gln Gln Leu Leu Asp
            20

<210> SEQ ID NO 3
<211> LENGTH: 10
<212> TYPE: PRT

<213> ORGANISM: Triticum sp.

<400> SEQUENCE: 3

Ile Tyr Ile Pro Val Gln Cys Pro Ala Thr
1               5                   10

<210> SEQ ID NO 4
<211> LENGTH: 13
<212> TYPE: PRT
<213> ORGANISM: Triticum sp.

<400> SEQUENCE: 4

Thr Val Pro Phe Pro His Thr Pro Val Gln Lys Pro Thr
1               5                   10

<210> SEQ ID NO 5
<211> LENGTH: 16
<212> TYPE: PRT
<213> ORGANISM: Triticum sp.

<400> SEQUENCE: 5

Gly Glu Gln His Ser Ser Cys Gln Thr Val Gln His Gln Cys Cys Arg
1               5                   10                  15

<210> SEQ ID NO 6
<211> LENGTH: 17
<212> TYPE: PRT
<213> ORGANISM: Triticum sp.

<400> SEQUENCE: 6

Ala Ile Gln Ser Val Glu Glu Ala Ile Ile Gln Gln Gln Pro Gln Gln
1               5                   10                  15

Gln

<210> SEQ ID NO 7
<211> LENGTH: 260
<212> TYPE: PRT
<213> ORGANISM: Triticum sp.

<400> SEQUENCE: 7

Leu Glu Thr Ile Cys Ser Gln Gly Phe Gly Gln Cys Gln His His Gln
1               5                   10                  15

Gln Leu Gly Gln Gln Leu Leu Asp Gln Met Lys Pro Cys Val Ala
                20                  25                  30

Phe Val Gln His Gln Cys Ser Pro Val Arg Thr Pro Phe Pro Gln Thr
                35                  40                  45

Arg Gly Glu Gln His Ser Ser Cys Gln Thr Val Gln His Gln Cys Cys
            50                  55                  60

Arg Gln Leu Val Gln Ile Pro Glu Gln Ala Arg Cys Lys Ala Ile Gln
65                  70                  75                  80

Ser Val Glu Glu Ala Ile Ile Gln Gln Gln Pro Gln Gln Trp Asn
                85                  90                  95

Glu Pro Gln Gln Glu Ala His Leu Lys Ser Met Arg Met Ser Leu Gln
            100                 105                 110

Thr Leu Pro Ser Met Cys Asn Ile Tyr Val Pro Val Gln Cys Gln Gln
            115                 120                 125

Gln Gln Gln Leu Gly Arg Gln Gln Gln Gln Leu Gln Glu Gln Leu
        130                 135                 140

Lys Pro Cys Ala Thr Phe Leu Gln His Gln Cys Arg Pro Met Thr Val
145                 150                 155                 160

```
Pro Phe Pro His Thr Pro Val Gln Lys Pro Thr Ser Cys Gln Asn Val
                165                 170                 175

Gln Ser Gln Cys Cys Arg Gln Leu Ala Gln Ile Pro Glu Gln Phe Arg
            180                 185                 190

Cys Gln Ala Ile His Asn Val Val Glu Ser Ile Arg Gln Gln Gln His
        195                 200                 205

His Gln Pro Gln Gln Glu Val Gln Leu Glu Gly Leu Arg Met Ser Leu
    210                 215                 220

His Thr Leu Pro Ser Met Cys Lys Ile Tyr Ile Pro Val Gln Cys Pro
225                 230                 235                 240

Ala Thr Thr Thr Thr Pro Tyr Ser Ile Thr Met Thr Ala Ser Tyr Thr
                245                 250                 255

Asp Gly Thr Cys
        260

<210> SEQ ID NO 8
<211> LENGTH: 783
<212> TYPE: DNA
<213> ORGANISM: Triticum sp.

<400> SEQUENCE: 8
ttggaaacca tatgtagcca gggcttcgga caatgccaac accaccaaca actagggcaa      60
caacagttgc tggatcagat gaagccatgt gtggctttcg tacaacatca gtgtagccca     120
gtgagaacac cattccccca aacacgggga gagcagcata gcagttgcca aaccgtgcaa     180
caccaatgct gtcggcagct agtgcagatc ccagaacaag cccggtgcaa ggccatacag     240
agcgtggaag aggctatcat tcaacaacag ccccaacaac aatggaatga ccccaacag      300 gaagcacacc ttaagagcat gaggatgtcg cttcagaccc tgccgtctat gtgcaacatc     360
tacgtcccgg tacaatgcca gcaacagcaa caactggggc gacaacaaca acaacagttg     420
caggagcagt taaaaccgtg tgcgacattc ctacaacatc aatgtaggcc aatgacagtg     480
ccattcccgc atacaccagt gcagaagccc accagctgcc agaacgtgca gtcccaatgc     540
tgccggcagc tagcacagat cccagagcaa ttccgctgcc aagccattca taatgtggta     600
gagtctatca ggcaacaaca acatcaccaa ccacaacagg aagtacaact tgagggcctg     660
aggatgtcac ttcacaccct accgtcgatg tgcaaaatct acatccctgt acaatgccca     720
gccaccacca ccaccccccta tagcattacc atgacagcta gctataccga tggtacctgc     780
tag                                                                   783
```

PROTEIN LIPASE INHIBITOR FOR FLOUR AND DOUGH

INCORPORATION BY REFERENCE

This application is a continuation-in-part application of international patent application Ser. No. PCT/IB2003/004585 filed Sep. 26, 2003 and published as WO 2004/029084 on Apr. 8, 2004, claiming priority from Great Britain patent application Ser. Nos. 0222512.6 filed Oct. 10, 2002 and 0223674.3 filed Dec. 2, 2002, and U.S. provisional application 60/431,209 filed Dec. 5, 2002.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to proteins. The present invention further relates to the isolation of and characterisation of a lipase inhibitor and its effect on different lipases. The present invention also relates to the use of a lipase inhibitor as a screen for lipases and/or the lipases identified by such a screen.

The present invention also relates to the use of the inhibitor and/or lipases identified by a lipase inhibitor in food and/or feed technologies.

The present invention also relates to the use of the inhibitor and/or lipases identified by a lipase inhibitor in detergents.

The present invention further relates to use of the inhibitor and/or lipases identified by a lipase inhibitor with flour, in particular, but not exclusively, with wheat flour. The present invention also relates to dough manufacture and flour dough based products and in particular, but not exclusively, to improving the strength and machinability of doughs and the volume, softness and crumb structure of bread and other baked products.

BACKGROUND OF THE INVENTION

Enzyme inhibitors are found in almost all kinds of living organism and particularly in plants. Inhibitors in plants are often important for the regulation of certain metabolic reactions. In particular, lipase inhibitors are also widely found in plants, particularly plants such as cereals.

In the last two decades research into lipase inhibitors has been carried out to evaluate lipase inhibitors for use in obesity treatments, and commercial products based on lipase inhibition with the aim to treat obesity are known.

Within food and feed technologies, lipase inhibitors have not gained much focus. However, with the increased application and use of enzymes in the food and/or feed industries, more attention has to be paid to the effect of endogenous or added inhibitors to the food. WO 00/39289, for example, discloses novel xylanase inhibitors.

Lipases (E.C. 3.1.1.X) have also been used directly in the food and/or feed industries, for example in foods and/or feeds comprising cereals and, in particular in bread production. For instance, in EP 0 585 988 it is claimed that lipase addition to dough resulted in an improvement in the antistaling effect. It is suggested that a lipase obtained from *Rhizopus arrhizus* when added to dough can improve the quality of the resultant bread when used in combination with shortening/fat. WO94/04035 teaches that an improved softness can be obtained by adding a lipase to dough without the addition of any additional fat/oil to the dough. Castello, P. ESEGP 89-10 December 1999 Helsinki, shows that exogenous lipases can modify bread volume. Thus, lipases (E.C. 3.1.1.X) which hydrolyse triacylglycerols are known to be advantageous for use in the baking industry.

Some lipases in addition to having a triglyceride hydrolysing effect, are capable of hydrolysing polar lipids such as glycolipids, e.g. digalactosyldiglyceride (DGDG), and phospholipids (see for instance WO01/39602).

The substrate for lipases in wheat flour is 1.5-3% endogenous wheat lipids, which are a complex mixture of polar and non-polar lipids. The polar lipids can be divided into glycolipids and phospholipids. These lipids are built up of glycerol esterified with two fatty acids and a polar group. The polar group contributes to surface activity of these lipids. Enzymatic cleavage of one of the fatty acids in these lipids leads to lipids with a much higher surface activity. It is well known that emulsifiers, such as DATEM, with high surface activity are very functional when added to dough.

It has also been found that under certain conditions the use of lipases (E.C. 3.1.1.X) in dough may have detrimental consequences, such as the production of off-flavours, a detrimental impact on yeast activity, and/or a negative effect on bread volume. The negative effect on bread volume is often called overdosing. Overdosing can lead to a decrease in gluten elasticity which results in a dough which is too stiff and thus results in reduced volumes. In addition, or alternatively, such lipases can degrade shortening, oil or milk fat added to the dough.

Very little research work has however been done in relation to the lipase inhibitors in flour, particularly wheat flour.

SUMMARY OF THE INVENTION

In one aspect, the present invention provides a novel lipase inhibitor.

In another aspect, the present invention provides an assay method for determining the effect of a lipase inhibitor on one or more lipases.

In another aspect, the present invention provides a nucleotide sequence encoding a novel lipase inhibitor.

The present invention provides, in another aspect, an assay method for determining the effect of a lipase inhibitor on one or more lipases for use in flour and/or dough.

In a further aspect, the present invention provides a screening method for screening one or more proteins, in particular enzymes, to determine the effect of a lipase inhibitor thereon, and in particular to identify proteins (particularly enzymes) which have a modified activity in response to the lipase inhibitor. In particular, but not exclusively, the lipase inhibitor can be used as a tool to develop new and better lipases.

The present invention provides, in a further aspect thereof, the use of a lipase inhibitor and/or an enzyme obtainable, preferably obtained, by a screening method utilising said lipase inhibitor.

In another aspect, the present invention provides the use of a lipase inhibitor to modify lipase activity in flour and/or dough, particularly flour dough based products.

In another aspect, the present invention provides the use of a lipase inhibitor to modify lipase activity in detergents.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

Figure 7:
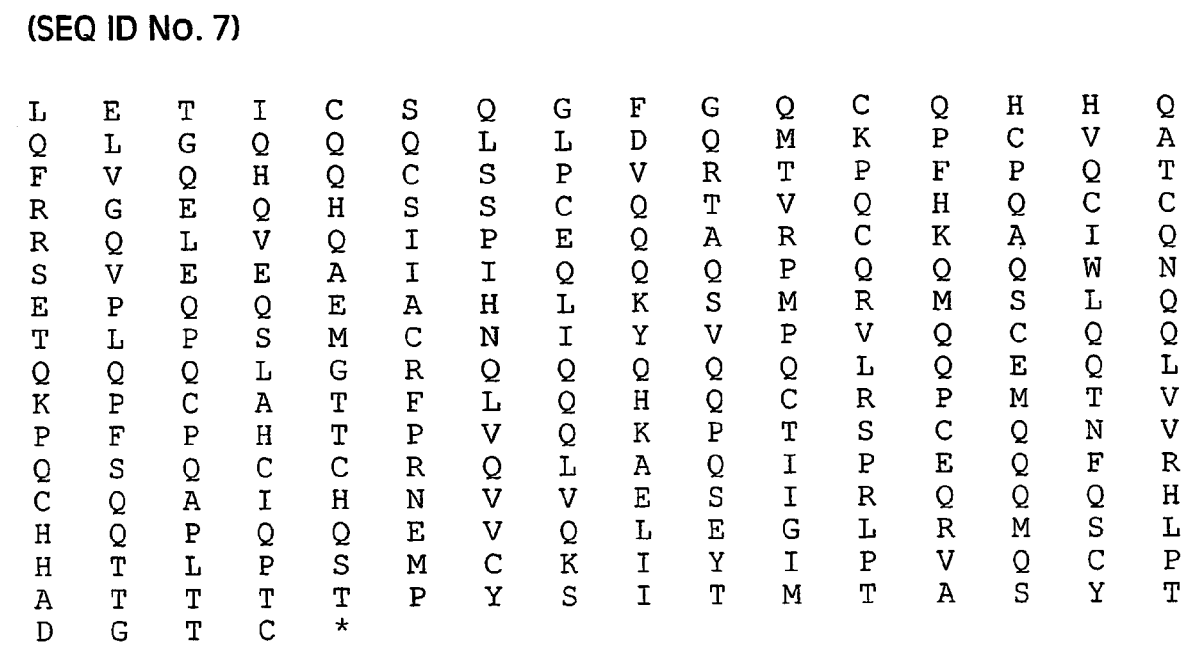

FIG. 7, which shows an amino acid sequence (SEQ ID No. 7) of a polypeptide (lipase inhibitor) according to the present invention;

FIG. 8, which shows a nucleotide sequence (SEQ ID No. 8) which encodes a polypeptide (lipase inhibitor) according to the present invention.

DETAILED DESCRIPTION

Figure 1:
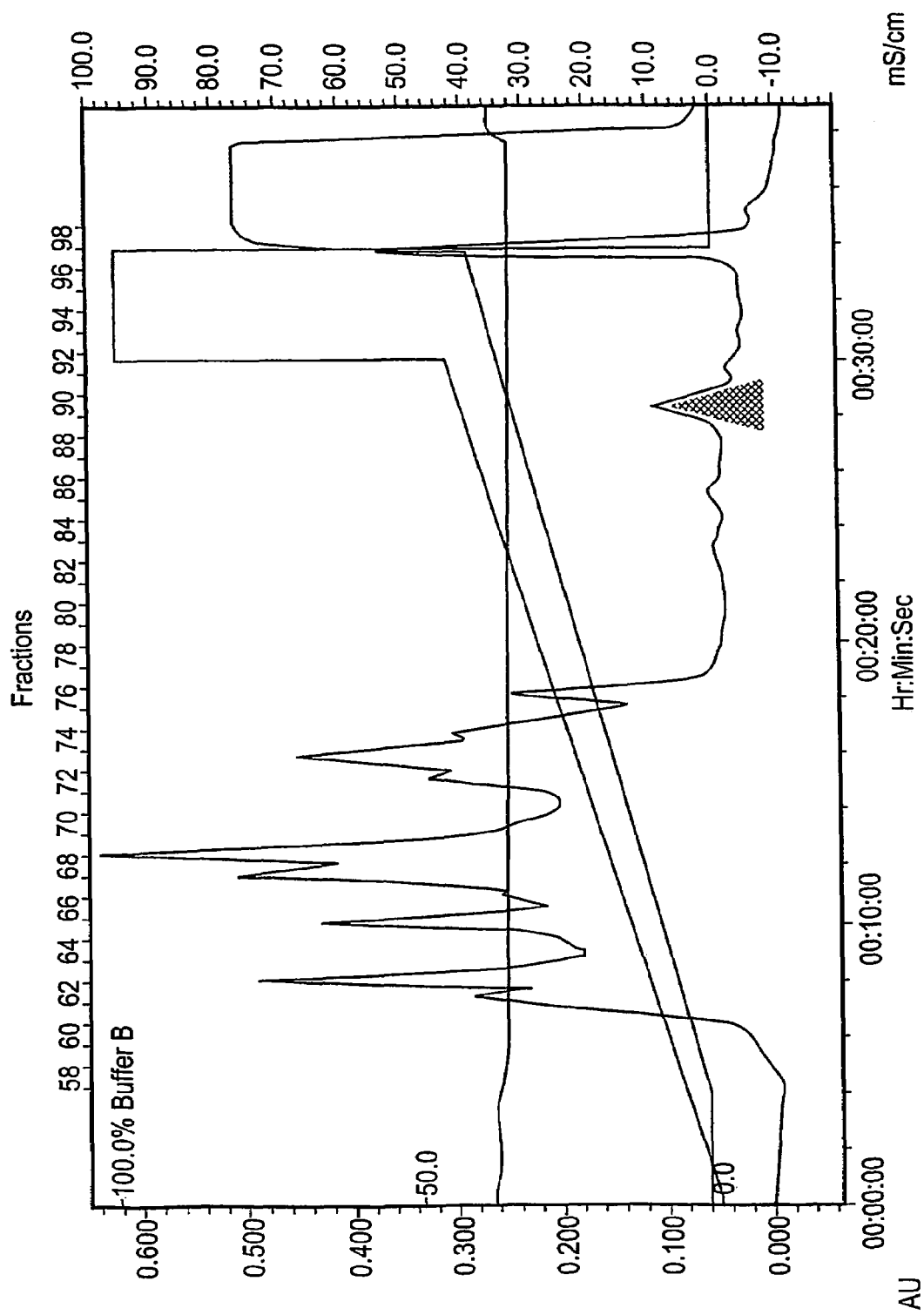
FIG. 1, which shows an elution profile of the Source S15, Ion Exchange Chromatography.

In a broad aspect, the present invention provides a lipase inhibitor comprising one or more of the amino acid sequences defined in SEQ ID No. 1, SEQ ID No. 2, SEQ ID No. 3, SEQ ID No. 4, SEQ ID No. 5 or SEQ ID No. 6 or an amino acid sequence which has at least 50% homology with any one of the amino acid sequences defined in SEQ ID No. 1, SEQ ID No. 2, SEQ ID No. 3, SEQ ID No. 4, SEQ ID No. 5 or SEQ ID No. 6.

In a further aspect, the present invention provides a lipase inhibitor comprising the amino acid sequences defined in SEQ ID No. 7 or an amino acid sequence which is at least 50% homologous with SEQ ID No. 7.

The present invention provides in one aspect a lipase inhibitor comprising SEQ ID No. 7 or an amino acid sequence having one or more deletions from, substitutions of or insertions to SEQ ID No. 7 wherein said amino acid sequence has at least 50%, preferably at least 60%, more preferably at least 70%, more preferably at least 75%, more preferably at least 85%, more preferably at least 90%, more preferably at least 95%, more preferably at least 98%, more preferably at least 99%, amino acid sequence identity or sequence homology with SEQ ID No. 7.

The present invention provides in another aspect a lipase inhibitor comprising one or more of the following:

SEQ ID No. 1, or an amino acid sequence having one or more deletions from, substitutions of or insertions to SEQ ID No. 1 wherein said amino acid sequence has at least 50%, preferably at least 60%, more preferably at least 70%, more preferably at least 75%, more preferably at least 85%, more preferably at least 90%, more preferably at least 95%, more preferably at least 98%, more preferably at least 99%, amino acid sequence identity or sequence homology with SEQ ID No. 1, SEQ ID No. 2, or an amino acid sequence having one or more deletions from, substitutions of or insertions to SEQ ID No. 2 wherein said amino acid sequence has at least 50%, preferably at least 60%, more preferably at least 70%, more preferably at least 75%, more preferably at least 85%, more preferably at least 90%, more preferably at least 95%, more preferably at least 98%, more preferably at least 99%, amino acid sequence identity or sequence homology with SEQ ID No. 2, SEQ ID No. 3, or an amino acid sequence having one or more deletions from, substitutions of or insertions to SEQ ID No. 3 wherein said amino acid sequence has at least 50%, preferably at least 60%, more preferably at least 70%, more preferably at least 75%, more preferably at least 85%, more preferably at least 90%, more preferably at least 95%, more preferably at least 98%, more preferably at least 99%, amino acid sequence identity or sequence homology with SEQ ID No. 3, SEQ ID No. 4, or an amino acid sequence having one or more deletions from, substitutions of or insertions to SEQ ID No. 4 wherein said amino acid sequence has at least 50%, preferably at least 60%, more preferably at least 70%, more preferably at least 75%, more preferably at least 85%, more preferably at least 90%, more preferably at least 95%, more preferably at least 98%, more preferably at least 99%, amino acid sequence identity or sequence homology with SEQ ID No. 4, SEQ ID No. 5, or an amino acid sequence having one or more deletions from, substitutions of or insertions to SEQ ID No. 5 wherein said amino acid sequence has at least 50%, preferably at least 60%, more preferably at least 70%, more preferably at least 75%, more preferably at least 85%, more preferably at least 90%, more preferably at least 95%, more preferably at least 98%, more preferably at least 99%, amino acid sequence identity or sequence homology with SEQ ID No. 5, SEQ ID No. 6, or an amino acid sequence having one or more deletions from, substitutions of or insertions to SEQ ID No. 6 wherein said amino acid sequence has at least 50%, preferably at least 60%, more preferably at least 70%, more preferably at least 75%, more preferably at least 85%, more preferably at least 90%, more preferably at least 95%, more preferably at least 98%, more preferably at least 99%, amino acid sequence identity or sequence homology with SEQ ID No. 6.

The present invention provides in another aspect a lipase inhibitor comprising one or more of the following:

SEQ ID No. 1, or an amino acid sequence having one or more deletions from, substitutions of or insertions to SEQ ID No. 1 wherein said amino acid sequence has at least 50% amino acid sequence identity or sequence homology with SEQ ID No. 1, SEQ ID No. 2, or an amino acid sequence having one or more deletions from, substitutions of or insertions to SEQ ID No. 2 wherein said amino acid sequence has at least 50% amino acid sequence identity or sequence homology with SEQ ID No. 2, SEQ ID No. 3, or an amino acid sequence having one or more deletions from, substitutions of or insertions to SEQ ID No. 3 wherein said amino acid sequence has at least 50% amino acid sequence identity or sequence homology with SEQ ID No. 3, SEQ ID No. 4, or an amino acid sequence having one or more deletions from, substitutions of or insertions to SEQ ID No. 4 wherein said amino acid sequence has at least 50% amino acid sequence identity or sequence homology with SEQ ID No. 4, SEQ ID No. 5 or an amino acid sequence having one or more deletions from, substitutions of or insertions to SEQ ID No. 5 wherein said amino acid sequence has at least 50% amino acid sequence identity or sequence homology with SEQ ID No. 5, SEQ ID No. 6, or an amino acid sequence having one or more deletions from, substitutions of or insertions to SEQ ID No. 6 wherein said amino acid sequence has at least 60%, more preferably at least 65%, more preferably at least 70%, amino acid sequence identity or sequence homology with SEQ ID No. 6.

The present invention provides in another aspect a lipase inhibitor comprising one or more of the following:

SEQ ID No. 1, or an amino acid sequence having one or more deletions from, substitutions of or insertions to SEQ ID No. 1 wherein said amino acid sequence has at least 65% amino acid sequence identity or sequence homology with SEQ ID No. 1, SEQ ID No. 2, or an amino acid sequence having one or more deletions from, substitutions of or insertions to SEQ ID No. 2 wherein said amino acid sequence has at least 50% amino acid sequence identity or sequence homology with SEQ ID No. 2, SEQ ID No. 4, or an amino acid sequence having one or more deletions from, substitutions of or insertions to SEQ ID No. 4 wherein said amino acid sequence has at least 90% amino acid sequence identity or sequence homology with SEQ ID No. 4, SEQ ID No. 5 or an amino acid sequence having one or more deletions from, substitutions of or insertions to SEQ ID No. 5 wherein said amino acid sequence has at least 60% amino acid sequence identity or sequence homology with SEQ ID No. 5, SEQ ID No. 6, or an amino acid sequence having one or more deletions from, substitutions of or insertions to SEQ ID No. 6 wherein said amino acid sequence has at least 60%, more preferably at least 65%, more preferably at least 70%, amino acid sequence identity or sequence homology with SEQ ID No. 6.

The present invention provides, in a further aspect thereof, a lipase inhibitor comprising one or more of the amino acid sequences defined in SEQ ID No. 1, SEQ ID No. 2, SEQ ID No. 3, SEQ ID No. 4, SEQ ID No. 5 and SEQ ID No. 6.

Suitably, lipase inhibition may be determined by the "Lipase Assay" detailed below. In particular, the lipase inhibitor according to the present invention may suitably inhibit triacylglycerol lipases having the E.C. number 3.1.1.3 (according to the International Union of Biochemistry and Molecular Biology (IUBMB) recommendations for Enzyme Nomenclature (1992)).

Preferably, the lipase inhibitor according to the present invention has a molecular weight of about 28-29 kDa, for example 29 kDa±1.2 kDa, more preferably 29 kDa±0.5 kDa, even more preferably 29 kDa±0.1 kDa, as determined by SDS PAGE.

In one aspect, the lipase inhibitor according to the present invention has an isoelectric point (pI) of about 5.8, suitably of 5.8±0.5, preferably of 5.8±0.1.

Preferably, the lipase inhibitor according to the present invention comprises two or more, more preferably three or more, more preferably four or more, more preferably five or more, and more preferably six, of a), b), c), d), e) or f) (defined above).

Preferably, the lipase inhibitor according to the present invention is obtainable, preferably obtained, from a cereal plant or part thereof.

Preferably, the lipase inhibitor according to the present invention is obtainable, preferably obtained, from one or more of the following rye, wheat, durum wheat, triticale, barley, sorghum, oats, maize or rice.

Preferably, the lipase inhibitor according to the present invention is obtainable, preferably obtained, from wheat.

Preferably, the lipase inhibitor according to the present invention is obtainable, preferably obtained, from cereal flour.

Preferably, the lipase inhibitor according to the present invention is obtainable, preferably obtained, from one or more of the following rye flour, wheat flour, durum wheat flour, triticale flour, barley flour, sorghum flour, oat flour, maize flour or rice flour.

Preferably, the lipase inhibitor according to the present invention is obtainable, preferably obtained, from wheat flour.

In one aspect, the lipase inhibitor according to the present invention is not a lipase inhibitor obtainable, or obtained, from peony (*Paeoniae radix*).

In one embodiment, the lipase inhibitor according to the present invention is not a plant toxin.

In one aspect, the lipase inhibitor according to the present invention is not one or more of the following: a protamine, a histone, a purothionin, a purothionin analogue, a polylysine or a polyarginine.

The amino acid sequences identified as SEQ ID No.s 1, 2, 3, 4, 5 and 6 are detailed below:

```
EPQQEAHLKSMRMSLQTLPSMCNIYVPVQCQQQQQ   (SEQ ID No. 1)

ETICSQGFGQCQHHQQLGQQQLLD              (SEQ ID No. 2)

IYIPVQCPAT                            (SEQ ID No. 3)

TVPFPHTPVQKPT                         (SEQ ID No. 4)

GEQHSSCQTVQHQCCR                      (SEQ ID No. 5)

AIQSVEEAIIQQQPQQQ                     (SEQ ID No. 6)
```

SEQ ID No. 7 is detailed in FIG. 7 hereinbelow.

In one aspect, SEQ ID No. 2 represents the N-terminal sequence of the lipase inhibitor according to the present invention.

Preferably, the lipase inhibitor according to the present invention is isolated and/or pure.

Suitably, the lipase inhibitor according to present invention may be a recombinant polypeptide, i.e. a polypeptide prepared by use of recombinant DNA techniques.

According to another aspect, the present invention provides an assay method for determining the degree of resistance of a lipase to a lipase inhibitor, wherein the method comprises:

contacting a lipase of interest with a lipase inhibitor; and determining the extent to which the inhibitor inhibits (if at all) the activity of the lipase of interest.

According to another aspect, the present invention provides an assay method for determining the degree of resistance of a lipase to a lipase inhibitor according to the present invention, wherein the method comprises:

contacting a lipase of interest with a lipase inhibitor according to the present invention; and determining the extent to which the inhibitor inhibits (if at all) the activity of the lipase of interest.

Suitably, the "Lipase Assay (PNP-acetate)" or the "Lipase Assay (tributyrin)" as defined hereinbelow may be used as suitable assays to determine the degree of resistance of a lipase to a lipase inhibitor according to the present invention.

According to a further aspect, the present invention provides a screening method for identifying lipases with an appropriate degree of resistance to a lipase inhibitor, wherein the method comprises:

contacting one or more proteins, preferably enzymes, preferably lipases, of interest with a lipase inhibitor;

determining the extent to which the inhibitor inhibits (if at all) the activity of the protein of interest;

identifying one or more proteins having a high or medium or low degree of resistance to the inhibitor;

preparing a quantity of those one or more proteins.

According to one aspect, the present invention provides a screening method for identifying lipases with an appropriate degree of resistance to a lipase inhibitor according to the present invention, wherein the method comprises:

contacting one or more proteins, preferably enzymes, preferably lipases, of interest with a lipase inhibitor according to the present invention;

determining the extent to which the inhibitor inhibits (if at all) the activity of the protein of interest;

identifying one or more proteins having a high or medium or low degree of resistance to the inhibitor;

preparing a quantity of those one or more proteins.

Suitably, the lipase inhibitor utilised in the screening method according to the present invention may be immobilised.

According to another aspect, the present invention provides a method comprising:

contacting one or more proteins, preferably enzymes, preferably lipases, of interest with a lipase inhibitor;

determining the extent to which the inhibitor inhibits (if at all) the activity of the protein of interest;

identifying one or more proteins having a high or a medium or a low degree of resistance to the inhibitor;

preparing a foodstuff, a dough for example, comprising the one or more identified proteins.

According to another aspect, the present invention provides a method comprising:

contacting one or more proteins, preferably enzymes, preferably lipases, of interest with a lipase inhibitor according to the present invention;

determining the extent to which the inhibitor inhibits (if at all) the activity of the protein of interest;

identifying one or more proteins having a high or a medium or a low degree of resistance to the inhibitor;

preparing a foodstuff, a dough for example, comprising the one or more identified proteins.

Suitably, the lipase inhibitor utilised in the methods according to the present invention may be immobilised.

Immobilisation of a lipase inhibitor can be performed on different solid supports with different surface properties. Various polymers in the form of beads, such as Agarose, alginate and chitosan from different manufacturers can be selected to immobilise the inhibitor by carrier binding, cross linking or entrapment. Ceramic or silica matrixes can also be used for immobilising the inhibitor. Amersham Biosciences is a manufacturer of a wide range of products which can be used for the immobilisation of a lipase inhibitor, such as NHS-activated Sepharose 4, CnBr-activated Sepharose 4, CnBr-activated Sepharose 4B, activated CH Sepharose 4B, ECH Sepharose 4B, Epoxy-activated Sepharose 6B, EAH Sepharose 4B, Thiopropyl Sepharose 6B and activated thiol Sepharose 4B. The immobilisation of the inhibitor may be performed on different types of non-ionic adsorbent resins manufactured by Rohm & Haas for example, such as Amberlite FPA58, Amberlite IRC50, Amberlite XAD7HP, Amberlite XAD761 and Duolite A7.

Suitably, the methods according to the present invention utilise a lipase inhibitor to identify proteins, in particular lipases, which are not inhibited by the lipase inhibitor (i.e. have a high resistance to the inhibitor) or are only inhibited to a low degree (i.e. are not that resistant to the inhibitor). Thus, lipases that will not be inhibited by for example endogenous lipase inhibitors in, for example, flour, such a wheat flour, can be identified. In this way, "resistant" or "partially resistant" lipases can be identified which can be added to a medium (flour containing products for example, such a flour doughs, i.e. bread and baked products) in a lower concentration compared with the concentration at which other "less resistant" lipases would have to be added in order to achieve the same effects.

Suitably, the methods according to the present invention utilise a lipase inhibitor to identify proteins, in particular lipases, which are inhibited by the lipase inhibitor (i.e. which have a low resistance to the inhibitor or which are susceptible to the inhibitor). In this way, lipases that will be inhibited by the lipase inhibitor can be identified. Thus, the inhibitor may be, for example, added to flour to prevent deterioration of the flour (from endogenous "susceptible" lipases for example) during storage.

Suitable identified lipases can then be used to prepare a foodstuff, in particular a dough and bakery products.

Suitably, identified lipases for use in the preparation of a foodstuff, in particular a dough and/or a bakery product, have a high degree of resistance to the lipase inhibitor, i.e. are not inhibited or only inhibited to a low degree by the lipase inhibitor.

Suitably, the methods according to the present invention utilise the lipase inhibitor according to the present invention.

Suitably, the methods according to the present invention may utilise a lipase inhibitor obtainable from, preferably obtained from, a cereal, in particular wheat. In particular, the methods according to the present invention may utilise a lipase inhibitor obtainable from, preferably obtained from, cereal flour, in particular wheat flour. Suitably, the methods according to the present invention may utilise a lipase inhibitor obtainable from, preferably obtained from, a plant or a plant flour other than wheat. Suitably, other plants may be for example rye, barley, triticale, maize, oats, soya and rice. By way of example only, suitable lipase inhibitors for use in the methods of the present invention are taught in JP 07025779 (namely a lipase inhibitor from rice embryo buds) and/or JP 03219872 (namely a lipase inhibitor isolated from *Nerima daikon*).

In a further aspect, by now knowing the chemical identity of the lipase inhibitor, workers can now determine the quantity of the inhibitor in, for example, a flour, such as a wheat flour. For convenience, we shall call this method the "Inhibitor Amount Determination Method".

The Inhibitor Amount Determination Method would enable workers to select one or more appropriate lipases for addition to the flour, suitably wheat flour, and/or select appropriate amounts of one or more lipases for addition to the flour, suitably wheat flour.

Thus, the present invention further provides a method comprising: (a) determining the amount or type of inhibitor in a flour, suitably a wheat flour; (b) selecting a suitable lipase for addition to the flour, suitably a wheat flour, and/or selecting a suitable amount of a lipase for addition to the flour, suitably a wheat flour; and (c) adding the suitable lipase and/or suitable amount of the lipase to the flour, suitably a wheat flour.

Furthermore, the present invention provides a method comprising: (a) determining the amount or type of inhibitor in a flour, suitably a wheat flour; (b) selecting a suitable flour, suitably a wheat flour, and/or selecting a suitable amount of flour, suitably wheat flour; and (c) adding the suitable flour, suitably wheat flour, and/or adding the suitable amount of the flour, suitably a wheat flour, to a dough.

Detection of the amount of inhibitor can be determined by standard chemical or physical techniques, such as by analysis of solid state NMR spectra. The amount of inhibitor may even be determined by use of lipase enzymes that are known to be detrimentally affected by the inhibitor. In this last aspect, it would be possible to take a sample of the wheat flour and add it to a known quantity of such a lipase. At a certain time point the activity of the lipase can be determined, which resultant activity can then be correlated to an amount of inhibitor in the wheat flour.

Thus, the present invention also encompasses the use of the combination of a lipase and the inhibitor as a means to calibrating and/or determining the quantity of inhibitor in a wheat flour sample.

Antibodies to the inhibitor can be used to screen wheat flour samples for the presence of the inhibitor of the present invention. The antibodies may even be used to isolate amounts of the inhibitor from a wheat flour sample.

In another aspect, the present invention provides a method of identifying and/or separating and/or purifying a lipase inhibitor from a plant extract, preferably a cereal extract, wherein the method comprises:

immobilising a lipase, preferably lipase 3 from *Aspergillus niger* as taught in EP 0 977 869, for example in an affinity chromatography column;

contacting the immobilised lipase with a plant extract, preferably a cereal extract;

identifying one or more lipase inhibitors with affinity for the immobilised lipase.

The immobilised lipase may be immobilised on different solid supports with different surface properties. Various polymers in the form of beads, such as Agarose, alginate and chitosan from different manufacturers can be selected to immobilise the lipase by carrier binding, cross linking or entrapment. Ceramic or silica matrixes can also be used for immobilising the lipase. Amersham Biosciences is a manufacturer of a wide range of products which can be used for the immobilisation of a lipase, such as NHS-activated Sepharose 4, CnBr-activated Sepharose 4, CnBr-activated Sepharose 4B, activated CH Sepharose 4B, ECH Sepharose 4B, Epoxy-activated Sepharose 6B, EAH Sepharose 4B, Thiopropyl Sepharose 6B and activated thiol Sepharose 4B.

The immobilisation of the lipase may be performed on different types of non-ionic adsorbent resins manufactured by Rohm & Haas for example, such as Amberlite FPA58, Amberlite IRC50, Amberlite XAD7HP, Amberlite XAD761 and Duolite A7. Various methods are available for immobilising ligands quickly, easily and safely through a chosen functional group. For example, CnBr-activated Sepharose 4B enables ligands comprising primary amino groups to be safely, easily and rapidly immobilised by a spontaneous reaction. The lipase is immobilised on a substrate in such a way so that the lipase retains its specific binding affinity for the substance of interest, namely the lipase inhibitor. Suitably, the lipase may exhibit specific and reversible binding affinity for the lipase inhibitor. In this way, the lipase inhibitor retained in the column can be eluted from the column by changing pH or salt or organic solvent concentration of the eluent.

An advantage of using an immobilised lipase is that easy, fast and specific separation of the lipase inhibitor from crude extract is provided. In addition, the use of immobilised lipase allows for reaction times to be controlled and to minimise inhibitor loss, in addition the immobilised lipase can be reused for may reaction cycles, thus lowering the overall production costs.

Here, the term "resistant" means that the activity of the lipase is not totally inhibited by the inhibitor. In other words, the inhibitor can be used in an assay/screen to identify lipases that are not detrimentally affected by the inhibitor.

Thus, the term "degree of resistance" in relation to the lipase vis-à-vis the lipase inhibitor is synonymous with the degree of non-inhibition of the activity of a lipase by the lipase inhibitor. Thus, a lipase that has a high degree of resistance to the lipase inhibitor is akin to a high degree of non-inhibition of a lipase by the lipase inhibitor.

In one aspect, the present invention provides the use of a lipase inhibitor in a foodstuff or feed. Preferably, the foodstuff or feed is a lipase containing foodstuff or feed. Preferably, the foodstuff or feed comprises wheat, preferably wheat flour. Suitably, the foodstuff may be one or more of a flour dough, bread, a baked product obtained from a flour dough.

In another aspect, the present invention provides the use of a lipase inhibitor in a detergent.

In a further aspect, the present invention provides the use of a lipase identifiable, preferably identified, by one or more of the methods according to the present invention in a foodstuff or feed.

In another aspect, the present invention provides the use of a lipase identifiable, preferably identified, by one or more of the methods according to the present invention in a detergent.

The present invention provides in accordance with a further aspect thereof a foodstuff or feed comprising a lipase inhibitor according to the present invention and/or a lipase identifiable, preferably identified, by one or more of the methods according to the present invention.

The present invention further provides in a further aspect thereof a detergent comprising a lipase inhibitor according to the present invention and/or a lipase identifiable, preferably identified, by one or more of the methods according to the present invention.

The present invention further encompasses the use in combination of a lipase and a lipase inhibitor. Suitably, the lipase may have more than one functionality and the lipase inhibitor may be capable of inhibiting, to a low, medium or high degree, one or more of these functionalities whilst not affecting or not significantly affecting the one or more other functionalities. By way of example only, the lipase may have one or more of the following activities: triacylglycerol lipase activity (E.C. 3.1.1.3); phospholipase A1 activity (E.C. 3.1.1.32); phospholipase A2 activity (E.C. 3.1.1.4); phospholipase B (or lysophospholipase) activity; galactolipase activity (E.C. 3.1.1.36). Suitably, the lipase inhibitor may be capable of inhibiting one or more of these activities. Preferably, the lipase inhibitor is capable of inhibiting at least triacylglycerol lipase activity. Suitably, the lipase inhibitor may be capable of inhibiting only triacylglycerol lipase activity.

In one aspect, the present invention provides a nucleotide sequence encoding the lipase inhibitor polypeptide according to the present invention.

In a further aspect, the present invention provides a nucleotide sequence selected from:

a nucleotide sequence comprising the nucleotide sequence identified as SEQ ID No. 8, or a nucleotide sequence which is at least 40%, preferably 50%, preferably 60%, more preferably 70%, preferably 80%, preferably 90%, preferably 95%, preferably 98%, homologous with SEQ ID No. 8;

a nucleotide sequence comprising the nucleotide sequence identified as SEQ ID No. 8, or the compliment thereof;

a nucleotide sequence capable of hybridising the nucleotide sequence identified as SEQ ID No. 8 or a fragment thereof;

a nucleotide sequence capable of hybridising to the complement of the nucleotide sequence identified as SEQ ID No. 8 or a fragment thereof; and a nucleotide sequence which is degenerate as a result of the genetic code to the nucleotides defined in (i), (ii), (iii) or (iv).

Preferably, the nucleotide sequence according to the present invention is linked to a promoter.

SEQ ID No. 8 is shown in FIG. 8.

Other aspects concerning the amino acid sequence of the present invention and/or the nucleotide sequence of the present invention include: a construct comprising or capable of expressing the sequences of the present invention; a vector comprising or capable of expressing the sequences of the present invention; a plasmid comprising or capable of expressing the sequences of the present invention; a tissue comprising or capable of expressing the sequences of the present invention; an organ comprising or capable of expressing the sequences of the present invention; a transformed host comprising or capable of expressing the sequences of the present invention; a transformed organism comprising or capable of expressing the sequences of the present invention. The present invention also encompasses methods of expressing the same, such as expression in a microorganism; including methods for transferring same.

The present invention further provides a method for producing a lipase inhibitor according to the present invention comprising cloning and expressing a nucleotide sequence, which nucleotide sequence encodes a lipase inhibitor in accordance with the present invention. In this way, a pure lipase inhibitor can be produced.

The term "wheat flour" as used herein is a synonym for the finely-ground meal of wheat. Preferably, however, the term means flour obtained from wheat per se and not from another grain. Thus, and unless otherwise expressed, references to "wheat flour" as used herein preferably mean references to wheat flour per se as well as to wheat flour when present in a medium, such as a dough.

In one embodiment the lipase inhibitor according to the present invention may have a pI of about 7.9. This pI has been calculated theoretically using http://us.expasy.org/tools/pi_tool.html and the amino acid sequence shown in SEQ ID No. 7.

Uses of the Lipase Inhibitor According to the Present Invention

In addition or alternatively to the uses of the lipase inhibitor according to the present invention detailed hereinbefore, one or more of the following uses are also contemplated:

Selective Inhibition of Lipases in Foodstuffs:

During the last decade there has been an increasing focus on the use of lipases in bread making, because it has been shown that lipases contribute to improved dough stability, and improved crumb structure of the bread. Different microbial lipases have been tested for their use in bread making.

The effect of lipases on endogenous lipids can be followed by the increase in free fatty acid in the dough during the mixing and fermentation of the dough. It has been observed that the activity of a lipase in dough cannot be easily predicted, because there is no correlation between the lipase units added to the dough, and the amount of fatty acid formed in the dough.

The results from using lipases in dough have shown that the formation of a certain amount of free fatty acid is advantageous, but formation of too much fatty acid produces a stiff dough and decreases the bread volume. The amount of free fatty acid formation under certain conditions may be controllable by the dosage of the lipase added to a dough.

On the other hand it has been shown that the type of lipid components hydrolysed in a dough is very important for the baking quality. Typically, one or more of the following lipid components may be present in a foodstuff: triacylglycerol lipids and breakdown products thereof; galactolipids and breakdown products thereof; phospholipids and breakdown products thereof.

It is envisaged that a lipase inhibitor may be added to a lipid containing foodstuff, for example a dough, to selectively prevent degradation of a desired lipid (by, for example, inhibiting the enzyme (lipase) involved in the degradation of that lipid) whilst allowing undesired lipids to be hydrolysed by the or another lipase (the activity of which is not affected by the inhibitor), which lipase(s) may be either naturally present in a dough or may be added to a dough. Such a preferred lipase inhibitor should prevent the hydrolysis of monoglycerides, digalactosyl monoglycerides (DGMGs) and lysophosphatidylcholin in a dough.

Reducing or Eliminating Lipase Activity in Flour:

Although lipases are beneficial in baking, it is known that endogenous lipases might be detrimental to the baking quality of wheat.

Undamaged wheat grains are normally stable to storage for a long period of time, as is white flour. However milled wholemeal flour is typically unstable in storage resulting in loss of nutritional value, reduced baking performance and oxidative rancidity. White flour may also contain residues of bran fragments and therefore also lipase activity that may deteriorate the baking quality of white flour.

This deterioration of the flour quality over time is caused by the action of a lipase on storage triacylglycerols (Biochemical Society Transactions (1998) 26(2) p. 152).

The lipase activity in wheat is located in the bran region, which is responsible for the hydrolysis of flour lipids. Wheat flour also contain a lipase in the endosperm but this enzyme is not active on insoluble triacylglycerol and therefore this enzyme is recognised as an esterase and will not play a major role in the lipid degradation during storage of flour.

It is thus envisaged that an inhibitor enzyme active against the bran lipase may be added to the flour to prolong the shelf life of wheat flour and especially wholemeal flour.

Obesity Treatment:

When a lipase inhibitor according to the present invention is added to a foodstuff, for example a dough, the lipase inhibitor is thermostable and is still active in bread after baking. Lipase inhibitors from wheat are active on pancreas lipase (Journal of Nutritional Science and Vitaminology (1995), 41(6), 699-706. ). Thus, the addition of the lipase inhibitor according to the present invention to a foodstuff, preferably a dough or a dough product, for example bread or baked products, can be used to prevent the digestion of lipids in the stomach. In addition, the lipase inhibitor according to the present invention may be used to suppress or inhibit lipolysis, prevent ingested lipids from being rapidly absorbed into the body, suppress the amount of the total absorbed fats and prevent hyperlipidemia and obesity by inhibiting activity of a lipolytic enzyme.

Use of the Lipase Inhibitor According to the Present Invention in Screening for Inhibited or Uninhibited Lipases:

Microorganisms, either transformed with a lipase gene or untransformed can be grown in media inducing lipase activity. The supernatants can be used directly or the lipase can be purified from the supernatant, and tested for lipase activity on relevant lipid substrates with and without the lipase inhibitor according to the present invention. The lipases showing the highest ratio between lipase activity in the presence of the inhibitor and lipase activity without the lipase inhibitor, are the most uninhibited.

Use of the Lipase Inhibitor According to the Present Invention in the Selection of Uninhibited Lipases:

Lipase inhibitors according to the present invention can be used as a substrate to screen for lipases with low or no (or high) inhibition.

By way of example only, a gene or population of genes encoding a lipase may be integrated into a plasmid transformed into a host organism, e.g. *Bacillus subtilis*. It is important that a signal sequence, either the lipase sequence's own or another, is placed in front of the lipase gene. The host microorganism is ideally low in lipase and protease productivity. The transformed population of microorganisms is plated on agar plates containing a minimal medium with a relevant lipid as carbon source and the lipase inhibitor. The transformants producing uninhibited lipases will have a higher growth rate than transformants producing inhibited lipases. Thereby it is possible to select uninhibited lipases (and inhibited lipases) based on colony size. Alternatively the uninhibited lipases can be selected based on halo size if the transformed population was plated on the above-mentioned medium containing an indicator for lipolytic activity, like Rhodamin B.

Alternatively, a population of different microorganisms can be plated on the above-mentioned medium, and microorganisms producing uninhibited lipases can be selected as described above.

Change of Substrate Specificity of Lipase by Adding Inhibitor:

Recently lipases have gained more widespread use in the food industry and especially in the baking industry. It has also been shown that lipases with activities on different substrates (for example one or more of triglycerides, phospholipids, galactolipids etc.) may be more beneficial than lipases with only one activity (for example on triglycerides only)—see for example EP 0977869 or EP 1108360.

When the lipase inhibitor according to the present invention is added to a dough in combination with a lipase with broad substrate specificity, the substrate specificity may be changed and a more preferable relative activity on different flour lipids may be obtained.

Coating of Inhibitor in Order to Stop Lipase Activity in Food when the Inhibitor is Released:

In food processing there is often the problem that the enzyme (lipase) is not only active during the processing of the food, but also thereafter. This problem can be overcome by adding a coated lipase inhibitor according to the present invention to the food product. During the food processing the coated inhibitor will have no effect on the lipase activity, and at the end of reaction the food item can then be heated to a temperature where the coating melts and the inhibitor is liberated. The inhibitor can then inhibit the lipase and prevent further lipase reaction in the food product.

Adding Inhibitor to Blanched Vegetable in Order to Improve Taste:

Blanching is one of the most important steps in food processing of various frozen vegetables. The primary objective of blanching is to inactivate undesirable enzymes, in particular lipases, that causes unfavourable effects in frozen vegetables.

Enzymes degrading phospholipids and galactolipids in vegetable seem to play an important role in the quality deterioration of vegetables and fruits (Mye-Jeong Kim et al, J. Agric. Food Chem. 2001, 49, 2241-2248). Some of these endogenous enzymes are quite difficult to inactivate during blanching. It is therefore envisaged to add a heat stable lipase inhibitor to vegetables during blanching in order to prevent lipid degradation during storage of the vegetables in order to improve and extend the quality of blanched frozen vegetables.

Inhibitor Active Only in the Water Phase of an Emulsion:

Most lipase reactions occur at the interphase between two immiscible liquid phases.

During enzyme reactions more polar lipids are formed. Lipase reaction on lipids containing polar lipids, such as phospholipids, will produce the corresponding lysophospholipid components which in a two-phase system will be transferred from the lipid phase to the water phase. In order to protect these preferred lyso-components from further hydrolysis, a lipase inhibitor according to the present invention may be added to the water phase. This will prevent further action from the lipase on the lysophospholipid components.

Inhibit Unwanted Lipase Activities in Lactic Acid Cultures:

Fermented (cultured) milk products are among the oldest milk products, resulting in early periods from natural contamination of milk with lactic acid bacteria and yeast. Lactic acid fermentation leads to the development of texture, pleasant taste, and improved storage quality of milk.

Traditional and industrial production of fermented dairy products uses specific bacterial cultures, known as starters. During the fermentation of milk, lactic acid bacteria produce lactic acid and also a number of enzymes, including lipases, which are excreted from the starter culture to the milk. Some of these lipases are preferable for the taste and flavour development, but others are not preferred in the milk product. Adding a specific lipase inhibitor according to the present invention, together with the lactic acid bacteria, to the milk may prevent the formation of unwanted lipase activity in the milk.

Use of Lipase Inhibitors in Accordance with the Present Invention in Combination with Detergents or Rinse Aids:

It is well known to use lipases in detergents and rinse aids, but the use of lipases for detergents has not been as widespread as first expected, because some lipase activity is left on the clothes after washing, and because lipase is active at low water activity it will react with available lipid dirt and create off-odours when wearing the clothes. This problem can be overcome if a lipase inhibitor is added to a wash softener, because the lipase will then work during washing, but in the last washing step the lipase will be inhibited.

Use of Lipase Inhibitors in Accordance with the Present Invention to Avoid Off-Odour Formation in Shoes or on Garments:

A lipase inhibitor according to the present invention may be added to shoes or other garments, which will limit the metabolization of lipids, and thereby reduce the formation of foul smelling compounds.

Use of Lipase Inhibitors in Accordance with the Present Invention to Deodorants:

It is also envisaged that the lipase inhibitors according to the present invention may be used in deodorants.

Isolated

In one aspect, preferably the polypeptide or protein is in an isolated form. The term "isolated" means that the sequence is at least substantially free from at least one other component with which the sequence is naturally associated in nature and as found in nature.

Purified

In one aspect, preferably the polypeptide or protein is in a purified form. The term "purified" means that the sequence is in a relatively pure state—e.g. at least about 90% pure, or at least about 95% pure or at least about 98% pure.

Cloning a Nucleotide Ssquence Encoding a Polypeptide According to the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labelled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence of the present invention.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers MH et al (1980) Nuc Acids Res Symp Ser 215-23 and Horn T et al (1980) Nuc Acids Res Symp Ser 225-232).

Amino Acid Sequences

The present invention also encompasses amino acid sequences of polypeptides having the specific properties as defined herein.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 µg of the freeze-dried material may be dissolved in 50 µl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen.

135 µl of water and 5 µg of endoproteinase Lys-C in 5 µl of water may be added to the above reaction mixture and the digestion may be carried out at 37° C. under nitrogen for 24 hours.

The resulting peptides may be separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA)

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software that can perform sequence comparisons include, but are not limited to, the BLAST package (see Ausubel et al 1999 Short Protocols in Molecular Biology, 4$^{th}$ Ed—Chapter 18), FASTA (Altschul et al 1990 J. Mol. Biol. 403-410) and the GENEWORKS suite of comparison tools. Both BLAST and FASTA are available for offline and online searching (see Ausubel et al 1999, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1):. 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses sequences that are complementary to sequences that are capable of hybridising under high stringency conditions or intermediate stringency conditions to nucleotide sequences encoding polypeptides having the specific properties as defined herein.

More preferably, the present invention encompasses sequences that are complementary to sequences that are capable of hybridising under high stringent conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC).

Site-Directed Mutagenesis

Once an enzyme-encoding nucleotide sequence and/or an amino acid sequence of the polypeptide has been isolated, it may be desirable to mutate the sequence in order to prepare a polypeptide having the desired properties of the present invention or to enhance the natural properties of the polypeptide.

Mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into enzyme-encoding nucleotide sequences is described in Nelson and Long (*Analytical Biochemistry* (1989) 180, p 147-151).

Furthermore, Sierks et al (Protein Eng (1989) 2, 621-625 and Protein Eng (1990) 3, 193-198) describes site-directed mutagenesis in *Aspergillus* glucoamylase.

Random Mutagenesis

Error prone PCR can be performed, for example by using the Diversify™ PCR Random Mutagenesis Kit from CLONTECH.

Localised Random Mutagenesis

A mutagenic primer (oligonucleotide) may be synthesised which corresponds to the part of the DNA sequence to be mutagenised except for the nucleotide(s) corresponding to amino acid codon(s) to be mutagenised. The primer will, in the 5' and 3' end, contain nucleotides corresponding to the sequence surrounding the sequence to be mutagenised. In the codons to be mutagenised different percentages of the four different nucleotides will be present at each position, giving the possibility for codons for different amino acids in the selected positions.

Subsequently, the resulting mutagenic primer may be used in a PCR reaction with a suitable opposite primer. The resulting PCR fragment may be cloned, perhaps after some additional modification, into a suitable vector, containing the rest of the coding region of the gene of interest.

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated in the genome of the organism. The term "incorporated" preferably covers stable incorporation into the genome.

The nucleotide sequence of the present invention or coding for a polypeptide having the specific properties as defined herein may be present in a vector, in which the nucleotide sequence is operably linked to regulatory sequences such that the regulatory sequences are capable of providing the expression of the nucleotide sequence by a suitable host organism, i.e. the vector is an expression vector.

The vectors of the present invention may be transformed into a suitable host cell as described below to provide for expression of a polypeptide having the specific properties as defined herein.

The choice of vector, e.g. plasmid, cosmid, virus or phage vector, will often depend on the host cell into which it is to be introduced.

The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

Thus, in a further embodiment, the invention provides a method of making nucleotide sequences of the present invention or nucleotide sequences encoding polypeptides having the specific properties as defined herein by introducing a nucleotide sequence into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB 110, pE194, pAMB1 and pIJ702.

Regulatory Sequences

In some applications, a nucleotide sequence for use in the present invention or a nucleotide sequence encoding a polypeptide having the specific properties as defined herein may be operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of heterologous regulatory regions, e.g. promoter, secretion leader and terminator regions.

Preferably, the nucleotide sequence of the present invention may be operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Host Cells

The term "host cell"—in relation to the present invention includes any cell that comprises either a nucleotide sequence encoding a polypeptide having the specific properties as defined herein or an expression vector as described above and which is used in the recombinant production of a polypeptide having the specific properties as defined herein.

Thus, a further embodiment of the present invention provides host cells transformed or transfected with a nucleotide sequence of the present invention or a nucleotide sequence that expresses a polypeptide having the specific properties as defined herein. The cells will be chosen to be compatible with the said vector and may for example be prokaryotic (for example bacterial), fungal, yeast or plant cells. Preferably, the host cells are not human cells.

Examples of suitable bacterial host organisms are gram negative bacterium or gram positive bacteria.

Depending on the nature of the nucleotide sequence encoding a polypeptide having the specific properties as defined herein, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells, such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

Organism

The term "organism" in relation to the present invention includes any organism that could comprise a nucleotide sequence according to the present invention or a nucleotide sequence encoding for a polypeptide having the specific properties as defined herein and/or products obtained therefrom.

Suitable organisms may include a prokaryote, fungus, yeast or a plant.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5674707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R.(Editors) *Aspergillus:* 50 years on. Progress in industrial microbiology vol 29. Elsevier Amsterdam 1994. pp. 641-666).

Gene expression in filamentous fungi has been reviewed in Punt et al. (2002) Trends Biotechnol 2002 May; 20(5): 200-6, Archer & Peberdy Crit Rev Biotechnol (1997) 17(4): 273-306.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5): 554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

Transformed Plants/Plant Cells

A host organism suitable for the present invention may be a plant. A review of the general techniques may be found in articles by Potrykus (*Annu Rev Plant Physiol Plant Mol Biol* [1991] 42:205-225) and Christou (Agro-Food-Industry Hi-Tech March/April 1994 17-27).

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Also, recombinant immunoglobulins may be produced as shown in U.S. Pat. No. 4,816,567.

Fusion Proteins

A polypeptide having the specific properties as defined herein may be produced as a fusion protein, for example to aid in extraction and purification thereof. Examples of fusion protein partners include glutathione-S-transferase (GST), 6×His, GAL4 (DNA binding and/or transcriptional activation domains) and (β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6(5):501-6.

In another embodiment of the invention, the amino acid sequence of a polypeptide having the specific properties as defined herein may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

The invention will now be further described by way of the following non-limiting examples.

EXAMPLES

Example 1

Isolation and Identification of a Lipase Inhibitor from Wheat

A lipase inhibitor was isolated from a commercial wheat flour (WF, Safeguard USA) according to the method described by Tani et al (Tani, H. Ohishi, H. and Watanabe, K (1994). Purification and characterisation of proteinous inhibitor of lipase from wheat flour. *J. Agric. Food Chem.* 42: 2382-2385) as follows:

180 g WF was suspended in 450 ml of 60% ethanol/water (V/V). This was done to remove lipids and other contaminants. After 20 minutes stirring at room temperature, the precipitated (pellets) material was then collected by 10 min. centrifugation at 10,000 g. The pellet was then solubilised in 380 ml of 50 mM Tris/HCl buffer, pH 7.4 by stirring at +4° C. for 18 hours. The undissolved material was then removed by 10 min. centrifugation at 10000 g.

The supernatant (LI) was then subjected to heat treatment at 85° C. for 4 min. After that the temperature was brought down to 4° C. by placing the bottle in an ice bath. The precipitated material was removed by 10 min centrifugation at 10,000 g, followed by filtration through a GF/F filter (Whatman, UK). 300 ml of filtrate was collected.

The filtrate was then concentrated on a rotary evaporator (Buchi, Rotavapor R-114) at 45° C. The precipitated material in the concentrated LI was removed by filtration through a GF/F filter. A 16 ml fraction was collected.

The concentrated LI was desalted on a Sephadex G25 column (XK50/28, 550 ml gel, Amersham Pharmacia biotech, Sweden) equilibrated in 20 mM NaAc, pH 4.6 (buffer A) with a flow rate of 10 ml/min. 25 ml of desalted LI was collected.

The desalted LI was applied to a Source S15 column (HR16/10, 20 ml gel, Amersham Pharmacia biotech, Sweden) equilibrated in buffer A. The LI was eluted with a 130 ml linear gradient from 0 to 0.5 M NaCl in buffer A at a flow rate of 4 ml/min during which 3 ml fractions were collected (FIG. 1). Fractions 89 and 90 (6 ml) were pooled and then concentrated (300 µl) on a 10 kDa VectaSpin 3 (Whatman, UK) ultra filtration unit.

Figure 2:
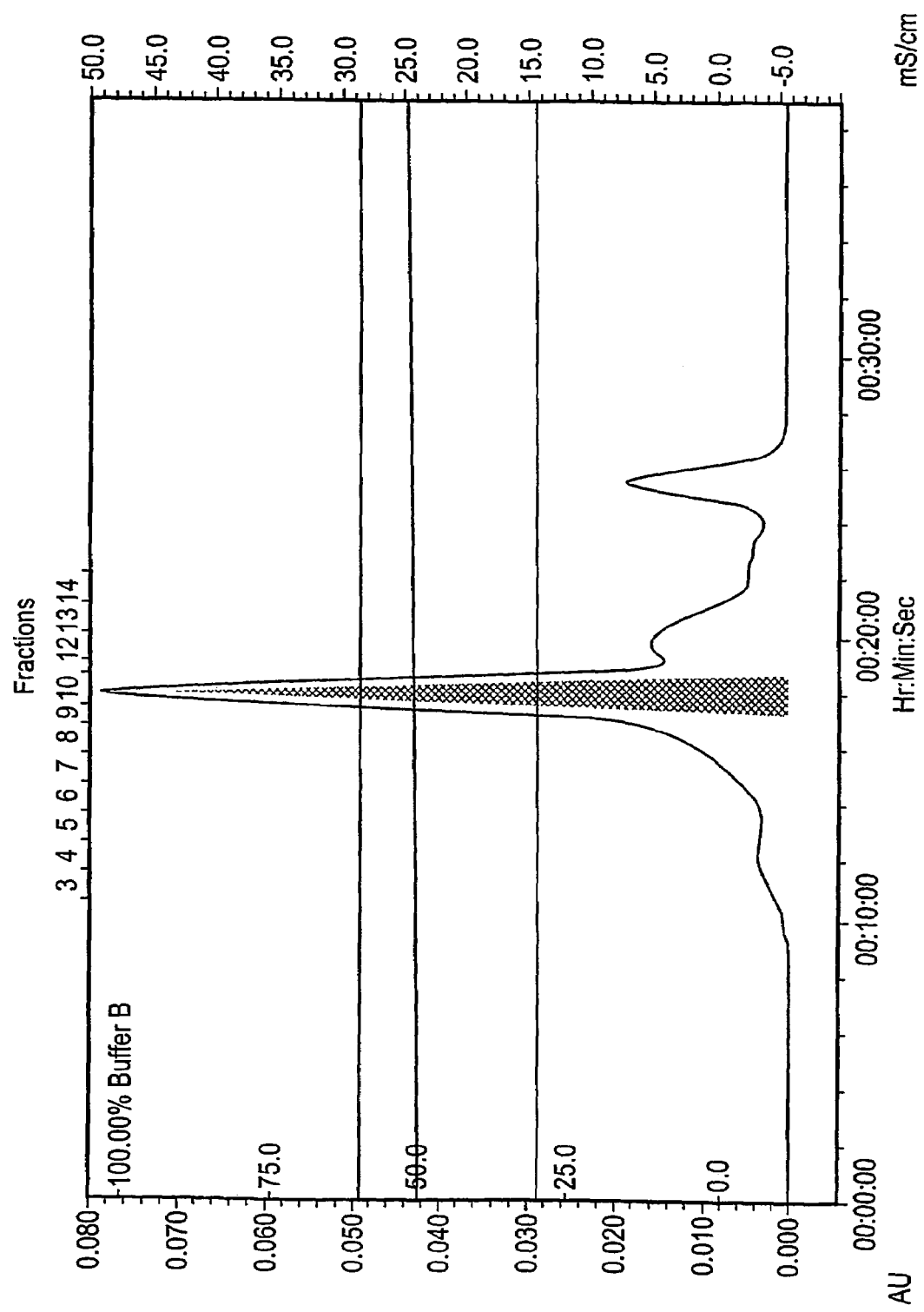
FIG. 2, which shows an elution profile of the GFC, Superdex 75. Gel Filtration Chromatography.

The resultant fraction was applied to a Superdex 75 column (HR10/30, 24 ml gel, Amersham Pharmacia biotech, Sweden) equilibrated in 20 mM NaAc, pH 5.5+0.3 M NaCl. The pure LI was eluted with a flow rate of 0.8 ml/min during which 400 µl fractions were collected (FIG. 2).

Figure 3:
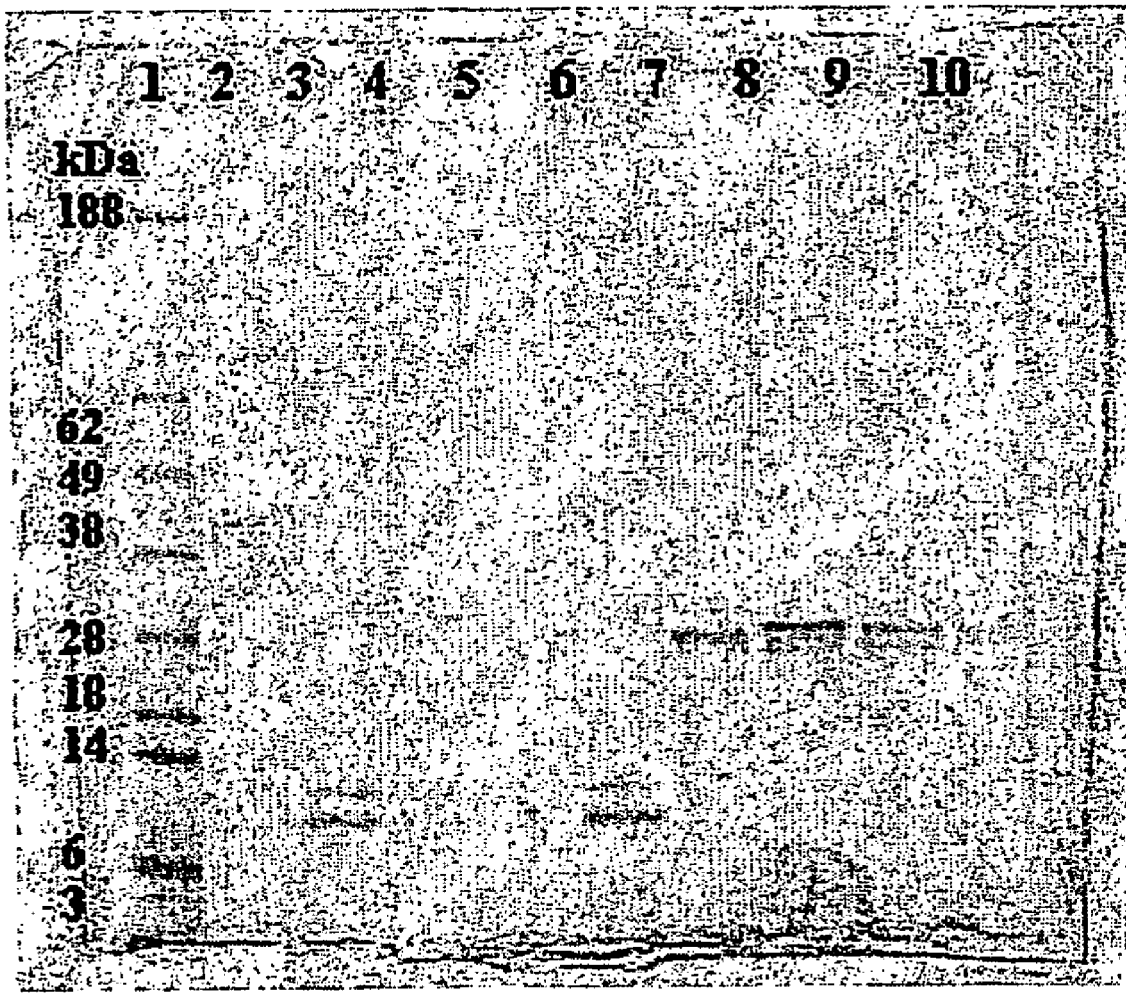
FIG. 3, which shows the determination of the purified supernatant (LI) [see Example 1 below] molecular weight by gel electrophoresis.

SDS-PAGE (Nu-PAGE, 4-12% Bis-Tris, MES running buffer, run according to manufacturers instructions manual, Novex, San Diego, Calif.) analysis of purified LI revealed three bands with molecular masses of approx. 29, 26 and 24 kDa in each of lanes 7-10 (see FIG. 3).

TABLE 1

Purification of lipase inhibitor from wheat flour

| Fraction | Protein mg/tot. | Activity LIU (PNP-acetate)/ tot. | Spec. activity LIU (PNP-acetate)/ mg | Purification factor | Yield % |
|---|---|---|---|---|---|
| Crude extract | 161.5 | 5426400 | 33600 | 1 | 100 |
| Heat treatment | 16.5 | 5454000 | 330545 | 9.8 | 100.5 |
| Ultra filt./desalting | 3.1 | 595000 | 191935 | 5.7 | 11 |
| Source S15 | 0.16 | 113220 | 707625 | 21.1 | 2.1 |
| Superdex 75 | 0.06 | 85680 | 1428000 | 42.5 | 1.6 |

Protein Assay

The assay was performed in a microtiter plate using Bio-Rad (Bio-Rad laboratories, Calif.) protein assay according to manufacturers instructions manual. Bovine serum albumin (Bio-Rad) was used as a standard.

"Lipase Assay (PNP-Acetate)" for the Determination of Lipase Inhibitor Activity Using PNP-Acetate as Substrate The assay was performed using p-nitro phenyl acetate (PNP-acetate, 0.5 mg/ml in 100 mM Na—P-buffer, pH 6.3) as a substrate. 50 µl of lipase (purified lipase from *Aspergillus niger*, Lip9704, 119 LIPU/ml [as taught in EP 0 977 869]) was supplemented with 5 or 8 µl of the lipase inhibitor in microtiter plates and mixed. The enzyme/inhibitor mixture was then pre-incubated at room temperature (25° C.) for 10 min. The enzyme assay was initiated by the addition of 200 µl of substrate and the mixture was incubated at 30° C. for 20 minutes with shaking. The control run contained all the components with buffer instead of lipase inhibitor and the blank run contained all the components with buffer instead of lipase inhibitor and lipase. The formation of PNP (p-nitrophenol) was measured at 405 nm.

One "LIU (Lipase Inhibitor Unit) (PNP-acetate)" is defined as the amount of inhibitor that reduced the lipase activity to half based on the "Lipase Assay (PNP-acetate)" detailed above. The measurement is based on the use of a lipase (Lipase 3) from *Aspergillus niger* as taught in EP 0 977 869.

Amino Acid Sequencing.

Purified lipase inhibitor was freeze-dried and 100 µg of the freeze-dried material was dissolved in 50 µl of a mixture of 8 M urea and 0.4 M ammonium hydrogen carbonate, pH 8.4. The dissolved protein was denatured and reduced for 15 minutes at 50° C. following overlay with nitrogen and addition of 5 µl 45 mM dithiothreitol. After cooling to room temperature, 5 µl of 100 mM iodoacetamide was added for the cysteine residues to be derivatized for 15 minutes at room temperature in the dark under nitrogen.

135 µl of water and 5 µg of endoproteinase Lys-C in 5 µl of water was added to the above reaction mixture and the digestion was carried out at 37° C. under nitrogen for 24 hours.

The resulting peptides were separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides were rechromatographed on a Develosil C18 column using the same solvent system, prior to N-terminal sequencing. Sequencing was done using an Applied Biosystems 476A sequencer using pulsed liquid fast cycles according to the manufacturer's instructions (Applied Biosystems, California, USA).

Lipase inhibitor fraction 10 from GFC Superdex 75 was sequenced and the following sequences were obtained

```
EPQQEAHLKSMRMSLQTLPSMCNIYVPVQCQQQQQ   (SEQ ID No. 1)

ETICSQGFGQCQHHQQLGQQQLLD              (SEQ ID No. 2)

IYIPVQCPAT                            (SEQ ID No. 3)

TVPFPHTPVQKPT                         (SEQ ID No. 4)

GEQHSSCQTVQHQCCR                      (SEQ ID No. 5)

AIQSVEEAIIQQQPQQQ                     (SEQ ID No. 6)
``` and SEQ ID No. 7 (see FIG. 7)

Example 2

Extraction of Lipase Inhibitor 200 gram wheat flour was mixed with 600 ml Ethanol/Water, 60/40 for 30 minutes. The mixture was centrifuged for 15 minutes at 18000 g. The supernatant was decanted and the pellets were re-dissolved in 500 ml TRIS-HCl, 10 mm pH 7.4 during stirring for 30 minutes and then centrifuged at 18000 g for 10 min. The supernatant was decanted and heated to boiling in a microwave oven. The product was cooled to ambient and filtered through a GF-A filter. The extracted lipase inhibitor was transferred to a round bottom flask and vacuum evaporated to 1/10 of the original volume.

"Lipase Assay (Tributyrin)" for the Determination of Lipase Inhibitor Activity Using Tributyrin as Substrate Lipase activity based on the use of tributyrin as substrate was measured as described in Food Chemical Codex, 4th edition, National Academy Press, 1996, p. 803 with the modification that samples were dissolved in deionised water instead of glycine buffer and that the pH-stat set point was 5.5 instead of 7.

This is because the pH in dough is 5.5 or approximately 5.5. LIPU is defined as the amount of enzyme that can liberate 1 µmol butyric acid per min. under the assay conditions Inhibitor activity of lipase inhibitors from wheat extracts were determined by LIPU assay of Lipase 3 from *Aspergillus niger* (see above and as taught in EP 0 977 969). The assay is made using increasing dosage of inhibitor and the inhibitor activity is determined as:

One "LIU (Lipase Inhibitor Unit) (tributyrin)" was defined as the amount of inhibitor needed to half 1 LIPU from the *Aspergillus niger* lipase based on the "Lipase Assay (tributyrin)" detailed above.

Effect of a Lipase Inhibitor According to the Present Invention from 3 Flours on the Activity of a Lipase from *Aspergillus niger*

The following flours were used:
Safe Guard (US)
Corde Noire (French)
Sølvmel (Danish)

The lipase inhibitor from each of these flours was produced according to the above-detailed procedure.

The effect of the inhibitor was tested using the Lipase assay (tributyrin) (detailed above).

Figure 4:
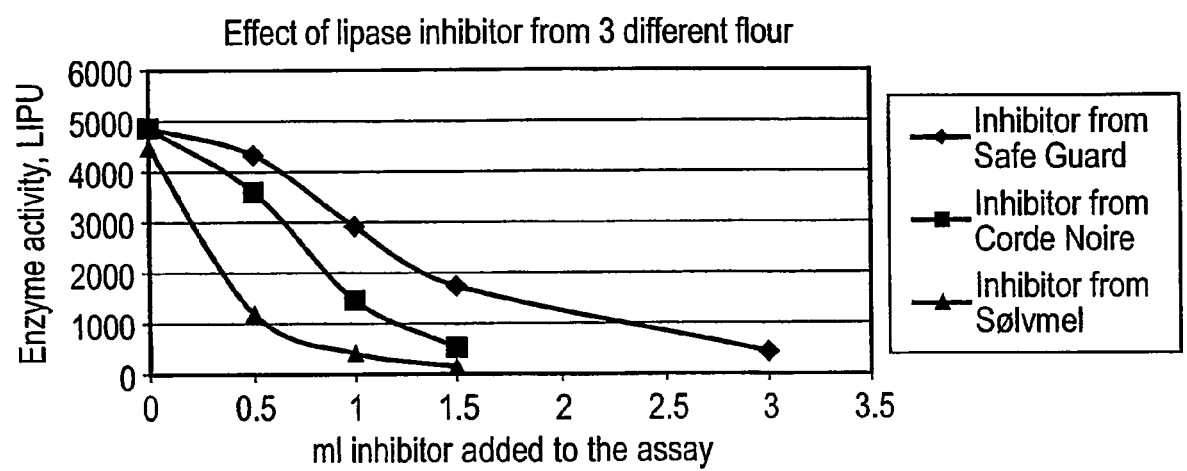
FIG. 4, which shows a graph of the effect of a lipase inhibitor isolated from three different wheat flours on lipase activity.

The results are shown in FIG. 4.

Based on the results shown in FIG. 4 the lipase inhibitor activity in the three different extracts was calculated (see Table 2).

TABLE 2

|  | LIU(tributyrin)/ml |
|---|---|
| Extract from Safe Guard | 8.3 |
| Extract from Corde Noire | 12.6 |
| Extract from Sølvmel | 28.7 |

The results confirm that the isolated inhibitor from wheat flour inhibits the activity of a lipase from *Aspergillus niger*, and the amount of lipase inhibitor varies from one flour to another.

Effect of Wheat Lipase Inhibitor on Different Lipases.

Use of lipase in bakery products has gained increased focus during the last decade. During the development of new lipases for baking it is of course important that the lipase has the right substrate activity against the flour lipids, but it is also important that the lipase is active in the flour and that the lipase is not too strongly inhibited by endogenous lipase inhibitors.

The impact of an endogenous lipase inhibitor isolated from wheat flour can be evaluated by measuring the activity of the enzyme as a function of inhibitor amount. In the following experiment four different lipases from *Thermomyces, Rhizopus, Fusarium* and *Aspergillus* were assayed for LIPU activity at increasing inhibitor concentration.

The inhibitor used was isolated from a Danish flour (Sølvmel) according to the procedure mentioned above. The results from the measurements are shown in FIG. 5.

Figure 5:
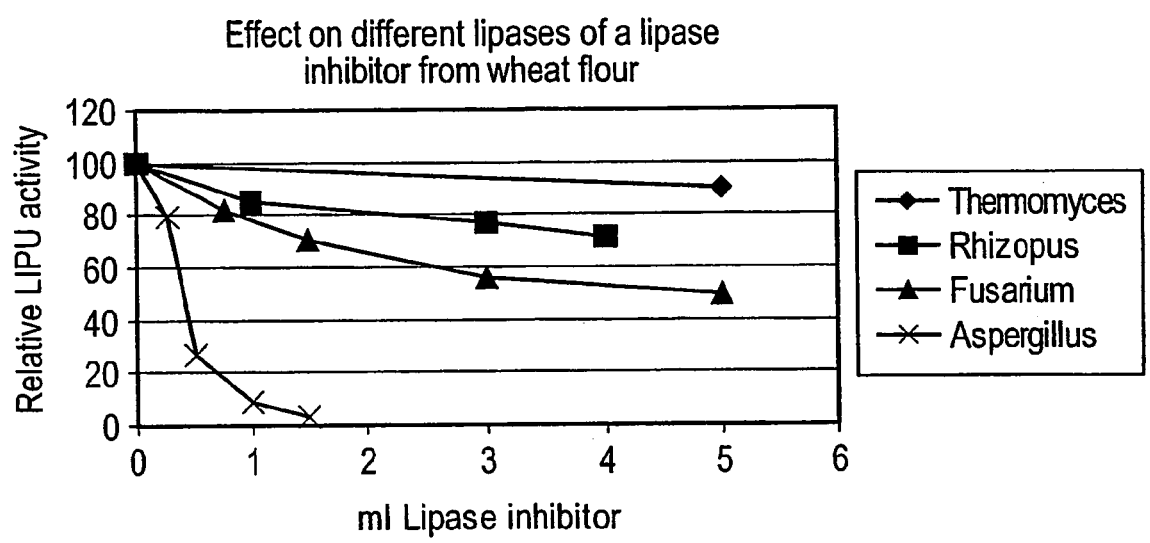
FIG. 5, which shows a graph of the effect of a lipase inhibitor from wheat flour on different lipases.

The results from FIG. 5 clearly demonstrate that lipase from *Aspergillus niger* is strongly inhibited by the isolated lipase inhibitor in wheat flour.

The inhibition of a lipase for use in baking is a very important quality parameter, because a lipase, which is strongly inhibited, should be added in a much higher concentration in order to obtain the same functionality on lipids in a dough.

The example demonstrates that the isolated lipase inhibitor from wheat flour can be used as an important tool in the development of new lipases for baking.

Heat Stability of Lipase Inhibitor.

The lipase inhibitor was isolated from Danish flour according to the procedure mentioned above. The inhibitor sample was divided into 2. One half was heat treated by boiling for 5 minutes and then cooled to ambient temperature.

Both inhibitor samples were tested in LIPU assay against lipase 3 from *Aspergillus niger*.

Figure 6:
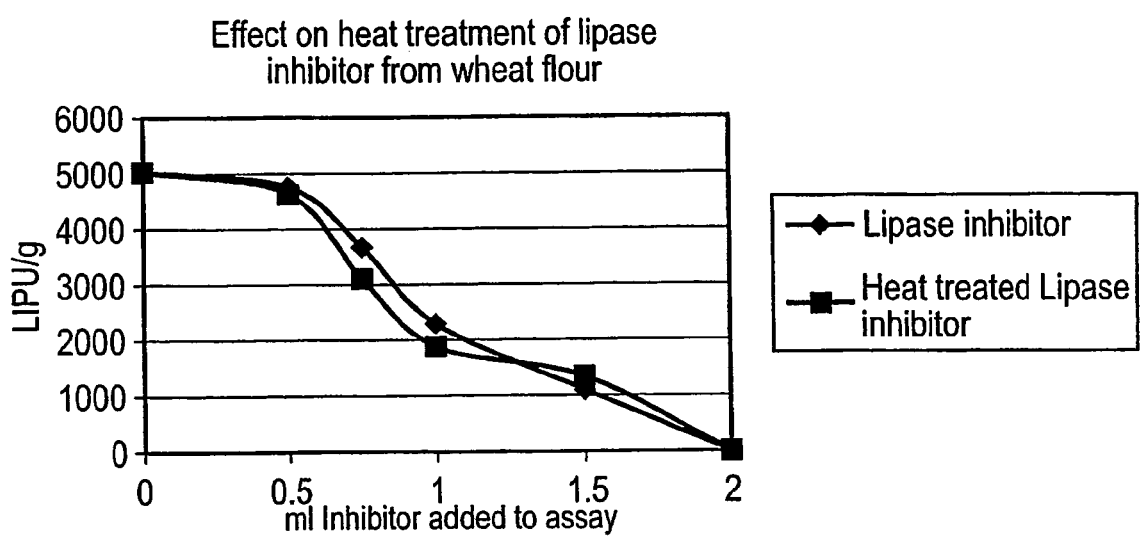
FIG. 6, which shows a graph of the effect of heat treatment of the lipase inhibitor from wheat flour on inhibition of a lipase.

The inhibition effect of the two samples are shown in FIG. 6.

As shown in FIG. 6 both inhibitor samples had the same inhibition effect on lipase 3 as a function of dosage, and it is concluded that the inhibitor remains stable after 5 minutes boiling.

Conclusion

A novel lipase inhibitor has been isolated from wheat flour. This inhibitor was sequenced. The lipase inhibitor can be used in the development of new lipases for baking, because the inhibition effect from the lipase inhibitor can be used as a selection criteria for lipases for baking.

Example 3

Determination of $K_i$ and $K_m$ for Purified Lipase 3 from *Aspergillus niger* p-Nitrophenol-Acetate Assay

Lipase activity was determined colorimetrically using p-nitrophenyl acetate as a substrate. In a microtiter plate was added 10 µl of sample or blank then 250 µl of substrate was added (0.5 mg p-nitrophenyl acetate/ml of 50 mM phosphate buffer, pH 6.5). The microtiterplate was incubated for 5 min. at 30° C. and the absorbance at 405 nm was then read in a microplate reader.

Purification of Lipase 3

A 60 ml sample of Grindlipase (Danisco A/S) a ferment of *Aspergillus niger*, pH 5.5 was first filtered through GF/B filter and then through 0.45 µm filter. The filtered sample was then desalted on a Superdex G25 SP column (430 ml, 22×5 cm) equilibrated in 20 mM triethanolamin, pH 7.3. Flow 5 ml/min. The total volume after desalting was 150 ml.

The desalted sample was applied to a Source Q30 anion exchange column (100 ml, 5×5 cm) equilibrated in 20 mM triethanolamine, pH 7.3. The column was washed with equilibration buffer until a stable baseline was obtained. Lipase activity was then eluted with a 420 ml linear gradient from 0 to 0.35 M NaCl in equilibration buffer, flow 5 m/min. Fractions of 10 ml were collected. 100 µl of 2M NaAc was added to each fraction to bring pH to 5.5. Fractions 26-32 (70 ml) were pooled.

To the pool from anion exchange was added ammonium sulfate to 1 M and the sample was applied to a Source Phenyl HIC column (20 ml, 10 x 2 cm) equilibrated in 20 mM sodium-acetate (pH 5.5), 1M $(NH_4)_2SO_4$. The column was washed in the equilibration buffer. Lipase was eluted with a 320 ml linear gradient from 1 M to 0 M $(NH_4)_2SO_4$ in 20 mM sodium-acetate (pH 5.5), followed by a wash with 20 mM sodium-acetate (pH 5.5), flow 1.5 m/min. Fractions of 7.5 ml were collected. Fractions 33-42 were kept. Fractions 33-41 were analyzed by SDS-PAGE and fraction 40 and 41 contained pure lipase.

Preparation of Lipase Inhibitor

Wheat flour (100 g) of commercial origin was extracted with 300 ml of 60% ethanol to eliminate endogenous lipids to which proteins might be adsorbed. The mixture was stirred for 20 min. and then centrifuged for 15 min. at 23,000 g. The resultant precipitate was homogenized in 250 ml 10 mM Tris-HCl (pH 7.4). After stirring for 20 min. the mixture was centrifuged for 10 min. at 15,000 g, then it was filtered on a 0.45 µm filter and subsequently concentrated 5 times on a rotary evaporator (according to Tani et al., (1994) Purification and characterization of proteinous inhibitor of lipase from wheat flour. *J. Agric. Food Chem.* 42: 2382-2385). One such extract, frozen in small portions, was used as lipase inhibitor throughout the experiments.

Inhibitory Activity

The inhibitory activity of the lipase inhibitor to various lipases was measured in the p-nitrophenyl acetate assay. Lipase plus inhibitor was preincubated for 5 min at 30° C. then the substrate was added and the remaining lipase activity was measured.

Data Reduction

Kinetic data were fitted to $v=V_{max}S/(K_m+S)$ where $V_{max}$ is maximum velocity, S is substrate concentration, and $K_m$ is the concentration giving half maximal rate (Michaelis constant), using the EZ-FIT curve-fitting microcomputer program [Perrella, (1988) EZ-FIT: A practical curve-fitting microcomputer program for the analysis of enzyme kinetic data on IBM-PC compatible computers. *Anal. Biochem.* 174: 437-447]. To determine $K_i$ the data were fitted to the formulas for non-competitive, competitive, un-competitive and the model showing the best fit (non-competitive) were used to determine $K_i$. The program uses the Nelder-Mead simplex optimization of initial guesses followed by Marquardt nonlinear regression algorithm for least squares optimization. Run's statistic is used to determine if the fitted curve goes through the data points or whether a systematic departure from the curve exists. The fitted parameter values and standard error are tested for significance by the Student t test.

Results and Discussion

Determination of $K_m$ for lipase with respect to p-nitrophenyl acetate has shown that the $K_m$ value is higher than the maximum solubility for p-nitrophenyl acetate under the conditions in the assay. This means that the determination of specific activity only is an approximate value.

Figure 9:
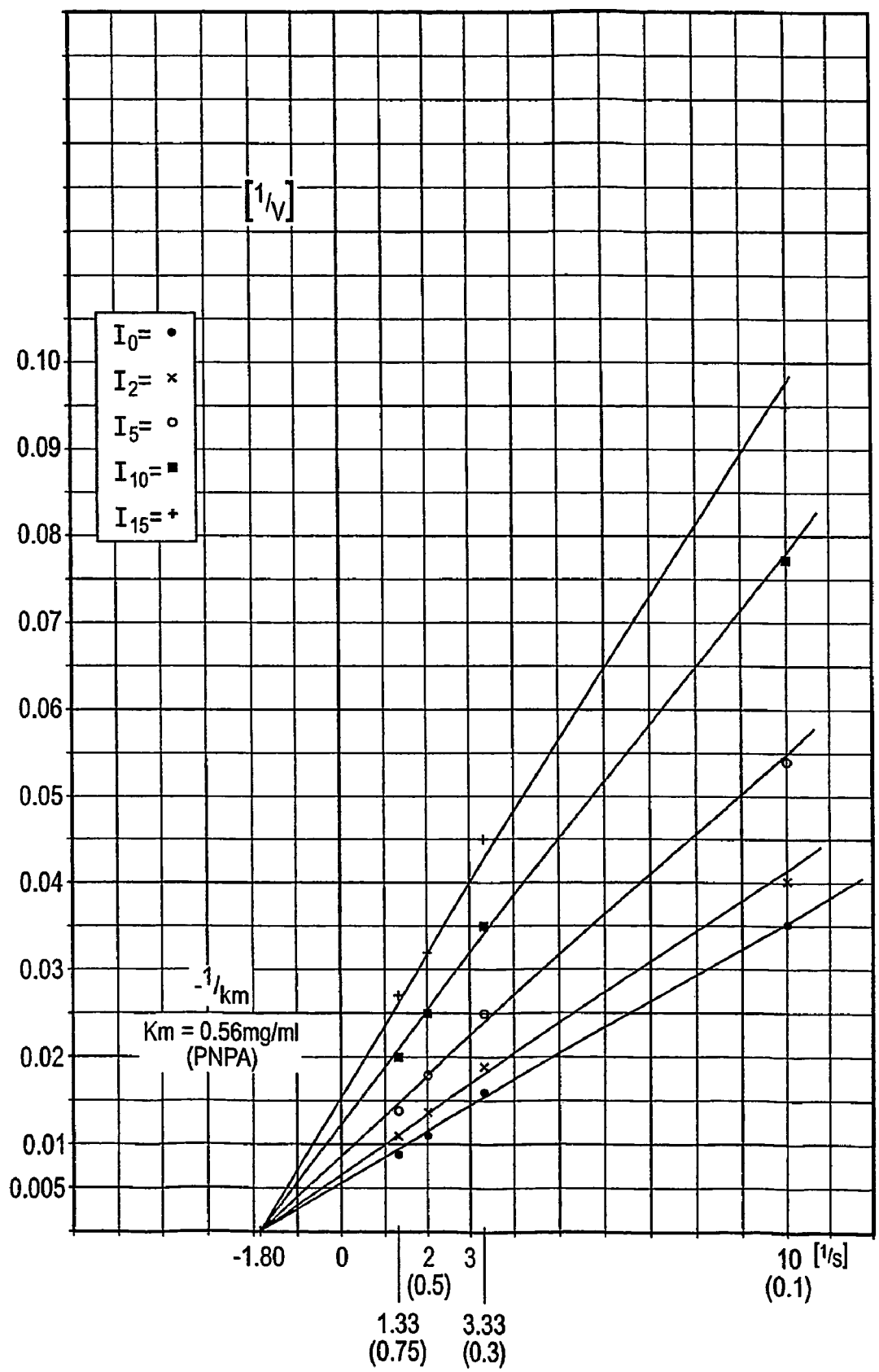
FIG. 9, which shows a Lineweaver-Burk double reciprocal plot of lipase activity as a function of p-nitrophenyl acetate concentrations in the absence or presence of different concentrations of wheat flour lipase inhibitor.

The initial rate of p-nitrophenyl acetate hydrolysis was determined at various concentrations of p-nitrophenyl acetate concentrations and at four levels of lipase inhibitor. The data had the best fit with a model for non-competitive inhibition. $K_m$ for p-nitrophenyl acetate was determined to be 0.67±0.04 mg/ml. $K_i$ for the inhibitor preparation described in materials and methods was determined to be 8.2±0.2 pl. See FIG. 9 for a Lineweaver-Burk plot of the data.

For a comparison $K_m$ and $K_i$ was determined for another commercial lipase (#1646). $K_m$ for p-nitrophenyl acetate was determined to be 2.0±0.6 mg/ml. $K_i$ for the inhibitor preparation described in Materials and Methods was determined to be 6.6±0.5 μl. The fit to non-competitive kinetics was, however, not accepted by the computer program (Runs test of residuals fails), this is because the $K_m$ value for lipase #1646 is so high that all the substrate values (between 0.1 and 0.75 mg/ml, which is maximum solubility) are situated at the very early steep part of the Michaelis-Menten curve, making a non-linear fit very poor.

$K_i$ is the concentration of inhibitor giving 50% inhibition of the enzyme. The lipase #1646 might therefore be slightly stronger inhibited than lipase 3 by the wheat flour inhibitor.

Conclusion

The inhibition of this lipase by a wheat flour inhibitor was shown to be non-competitive.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention is further described by the following numbered paragraphs:

1. A lipase inhibitor comprising SEQ ID No. 7 or an amino acid sequence having one or more deletions from, substitutions of or insertions to SEQ ID No. 7 wherein said amino acid sequence has at least 50% amino acid sequence identity or sequence homology with SEQ ID No. 7.

2. A lipase inhibitor comprising one or more of the following:
a) SEQ ID No. 1, or an amino acid sequence having one or more deletions from, substitutions of or insertions to SEQ ID No. 1 wherein said amino acid sequence has at least 50% amino acid sequence identity or sequence homology with SEQ ID No. 1,
b) SEQ ID No. 2, or an amino acid sequence having one or more deletions from, substitutions of or insertions to SEQ ID No. 2 wherein said amino acid sequence has at least 50% amino acid sequence identity or sequence homology with SEQ ID No. 2,
c) SEQ ID No. 3, or an amino acid sequence having one or more deletions from, substitutions of or insertions to SEQ ID No. 3 wherein said amino acid sequence has at least 50% amino acid sequence identity or sequence homology with SEQ ID No. 3,
d) SEQ ID No. 4, or an amino acid sequence having one or more deletions from, substitutions of or insertions to SEQ ID No. 4 wherein said amino acid sequence has at least 50% amino acid sequence identity or sequence homology with SEQ ID No. 4,
e) SEQ ID No. 5, or an amino acid sequence having one or more deletions from, substitutions of or insertions to SEQ ID No. 5 wherein said amino acid sequence has at least 50% amino acid sequence identity or sequence homology with SEQ ID No. 5,
f) SEQ ID No. 6, or an amino acid sequence having one or more deletions from, substitutions of or insertions to SEQ ID No. 6 wherein said amino acid sequence has at least 50% amino acid sequence identity or sequence homology with SEQ ID No. 6.

3. A lipase inhibitor according to paragraph 1 or paragraph 2, wherein said lipase inhibitor has a molecular weight of about 29 kDa, as determined by SDS PAGE.

4. A lipase inhibitor according to paragraph 2 or paragraph 3 when dependent upon paragraph 2, wherein said polypeptide comprises two or more of a), b), c), d), e) or f).

5. A lipase inhibitor according to any one of the preceding paragraphs wherein said polypeptide is obtainable from a cereal.

6. A lipase inhibitor according to any one of the preceding paragraphs wherein said polypeptide is obtainable from a flour.

7. An assay method for determining the degree of resistance of a lipase to a lipase inhibitor, wherein the method comprises:
(i) contacting a lipase of interest with a lipase inhibitor; and
(ii) determining the extent to which the inhibitor inhibits (if at all) the activity of the lipase of interest.

8. A screening method for identifying lipases with an appropriate degree of resistance to a lipase inhibitor, wherein the method comprises:
(i) contacting one or more proteins, preferably enzymes, preferably lipases, of interest with a lipase inhibitor;
(ii) determining the extent to which the inhibitor inhibits (if at all) the activity of the protein of interest;
(iii) identifying one or more proteins having a high or medium or low degree of resistance to the inhibitor;
(iv) preparing a quantity of those one or more proteins.

9. A method comprising:
(i) contacting one or more proteins, preferably enzyme, preferably lipases, of interest with a lipase inhibitor;
(ii) determining the extent to which the inhibitor inhibits (if at all) the activity of the protein of interest;

(iii) identifying one or more proteins having a high or a medium or a low degree of resistance to the inhibitor;

(iv) preparing a foodstuff comprising the one or more identified proteins.

10. A method according to any one of paragraphs 7, 8 or 9, wherein the lipase inhibitor is a lipase inhibitor according to any one of paragraphs 1-6.

11. A lipase obtainable from a method according to paragraph 7 or 8 or paragraph 10 when appended to paragraph 7 or paragraph 8.

12. Use of a lipase inhibitor according to any one of paragraphs 1 to 6 in a foodstuff or feed.

13. Use according to paragraph 12 wherein the foodstuff is a lipase containing foodstuff, such as dough, and/or dough products such as bread and/or baked products.

14. Use of a lipase identifiable by one or more of the methods according to paragraph 7 or paragraph 8 or paragraph 10 when appended to paragraph 7 or paragraph 8 in a foodstuff or feed.

15. A foodstuff or feed comprising a lipase inhibitor according to any one of paragraphs 1 to 6 and/or a lipase identifiable by one or more of the methods according to paragraphs 7 or 8 or paragraph 10 when appended to paragraph 7 or paragraph 8.

16. A nucleotide sequence encoding the lipase inhibitor polypeptide according to any one of paragraphs 1 to 6.

17. A nucleotide sequence selected from:

(i) a nucleotide sequence comprising the nucleotide sequence identified as SEQ ID No. 8, or a nucleotide sequence which is at least 40% homologous with SEQ ID No. 8;

(ii) a nucleotide sequence comprising the nucleotide sequence identified as SEQ ID No. 8, or the compliment thereof;

(iii) a nucleotide sequence capable of hybridising the nucleotide sequence identified as SEQ ID No. 8 or a fragment thereof;

(iv) a nucleotide sequence capable of hybridising to the complement of the nucleotide sequence identified as SEQ ID No. 8 or a fragment thereof; and (v) a nucleotide sequence which is degenerate as a result of the genetic code to the nucleotides defined in (i), (ii), (iii) or (iv).

18. A nucleotide sequence according to paragraph 16 or paragraph 17 wherein said nucleotide sequence is linked to a promoter.

19. A vector comprising the nucleotide sequence according to any one of paragraphs 16 to 18.

20. A transformed host cell comprising the nucleotide sequence according to any one of paragraphs 16 to 18.

21. A process of preparing a polypeptide according to any one paragraphs 1-6 comprising expressing a nucleotide sequence according to any one of paragraphs 16 to 18.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. An isolated lipase inhibitor comprising:
   (i) the amino acid sequence of SEQ ID No. 7; or
   (ii) an amino acid sequence having at least 90% amino acid sequence identity to SEQ ID No. 7, wherein said amino acid sequence functions as a lipase inhibitor.

2. A lipase inhibitor according to claim 1, wherein said lipase inhibitor has a molecular weight of about 29 kDa, as determined by SDS PAGE.

3. A lipase inhibitor according to claim 1 which is a polypeptide obtainable from a cereal.

4. A lipase inhibitor according to claim 1 which is a polypeptide obtainable from flour.

5. A foodstuff or feed comprising an isolated lipase inhibitor wherein the lipase inhibitor comprises:
   (i) the amino acid sequence of SEQ ID No. 7; or
   (ii) an amino acid sequence having at least 90% amino acid sequence identity to SEQ ID No. 7, wherein said amino acid sequence functions as a lipase inhibitor.

6. The lipase inhibitor according to claim 1, wherein the amino acid sequence has at least 95% sequence identity to SEQ ID No. 7.

7. The foodstuff or feed according to claim 5, wherein the amino acid sequence has at least 95% sequence identity to SEQ ID No. 7.

8. The lipase inhibitor according to claim 1, wherein the amino acid sequence has at least 98% sequence identity to SEQ ID No. 7.

9. The foodstuff or feed according to claim 5, wherein the amino acid sequence has at least 98% sequence identity to SEQ ID No. 7.

* * * * *